US007534567B2

(12) United States Patent
Albertson et al.

(10) Patent No.: US 7,534,567 B2
(45) Date of Patent: *May 19, 2009

(54) DETECTION OF NUCLEIC ACID SEQUENCE DIFFERENCES BY COMPARATIVE GENOMIC HYBRIDIZATION

(75) Inventors: Donna G. Albertson, Lafayette, CA (US); Daniel Pinkel, Lafayette, CA (US); Jane Fridyland, San Francisco, CA (US); Bing Huey, San Francisco, CA (US); Antoine Snijders, Antioch, CA (US); Joe W. Gray, San Francisco, CA (US); Anne Kallioniemi, Tampere (FI); Olli-Pekka Kallioniemi, Tampere (FI); Frederic Waldman, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 245 days.

This patent is subject to a terminal disclaimer.

(21) Appl. No.: 11/060,644

(22) Filed: Feb. 16, 2005

(65) Prior Publication Data

US 2006/0063168 A1    Mar. 23, 2006

Related U.S. Application Data

(63) Continuation-in-part of application No. 11/017,493, filed on Dec. 17, 2004, now Pat. No. 7,238,484, which is a continuation of application No. 09/644,140, filed on Aug. 22, 2000, now abandoned, which is a continuation of application No. 08/903,095, filed on Jul. 30, 1997, now Pat. No. 6,159,685, which is a continuation of application No. 08/468,629, filed on Jun. 6, 1995, now Pat. No. 5,721,098, which is a continuation of application No. 08/166,147, filed on Dec. 14, 1993, now abandoned, which is a continuation of application No. 07/969,948, filed on Oct. 30, 1992, now abandoned, which is a continuation-in-part of application No. 07/846,659, filed on Mar. 4, 1992, now abandoned.

(60) Provisional application No. 60/545,429, filed on Feb. 17, 2004.

(51) Int. Cl.
    *C12Q 1/68* (2006.01)
(52) U.S. Cl. ......................................................... 435/6
(58) Field of Classification Search ........................ None
    See application file for complete search history.

(56) References Cited

U.S. PATENT DOCUMENTS

| 4,358,535 A | 11/1982 | Falkow et al. |
| 4,647,529 A | 3/1987 | Rodland et al. |
| 4,666,828 A | 5/1987 | Gusella et al. |
| 4,681,840 A | 7/1987 | Stephenson et al. |
| 4,683,195 A | 7/1987 | Mullis et al. |
| 4,683,202 A | 7/1987 | Mullis |
| 4,707,440 A | 11/1987 | Stavrianopoulos |
| 4,710,465 A | 12/1987 | Weissman et al. |
| 4,711,955 A | 12/1987 | Ward et al. |
| 4,721,669 A | 1/1988 | Barton |
| 4,725,536 A | 2/1988 | Fritsch et al. |
| 4,770,992 A | 9/1988 | Van Den Engh et al. |
| 4,772,691 A | 9/1988 | Herman |
| 4,888,278 A | 12/1989 | Singer et al. |
| 4,981,783 A | 1/1991 | Augenlicht |
| 5,085,983 A | 2/1992 | Scanlon |
| 5,194,300 A | 3/1993 | Cheung |
| 5,348,855 A | 9/1994 | Dattagupta |
| 5,427,932 A | 6/1995 | Weier et al. |
| 5,447,841 A | 9/1995 | Gray et al. |
| 5,472,842 A | 12/1995 | Stokke et al. |
| 5,665,549 A * | 9/1997 | Pinkel et al. .................. 435/6 |
| 5,721,098 A * | 2/1998 | Pinkel et al. .................. 435/6 |
| 5,800,992 A | 9/1998 | Fodor et al. |
| 5,830,645 A | 11/1998 | Pinkel et al. |
| 5,837,196 A * | 11/1998 | Pinkel et al. ................ 422/55 |
| 5,840,484 A | 11/1998 | Seilhamer et al. |

(Continued)

FOREIGN PATENT DOCUMENTS

CA    2024769    3/1991

(Continued)

OTHER PUBLICATIONS

Beheshti et al. Chromosomal localization of DNA amplifications in neuroblastoma tumors using cDNA microarray comparative genomic hybridization. Neoplasia (2003) 5:53-62.*
Wolf et al. High-resolution analysis of gene copy number alterations in human prostate cancer using CGH on cDNA microarrays: impact of copy number on gene expression. Neoplasia (2004) 6:240-247.*
Wicker et al. A new look towards BAC-based array CGH through a comprehensive comparison with oligo-based array CGH. BMC Genomics (2007) 8:84, pp. 1-10.*
International Search Report and Written Opinion dated Jul. 26, 2006 issued in PCT/US05/05131.

(Continued)

*Primary Examiner*—Kenneth R. Horlick
*Assistant Examiner*—David C Thomas
(74) *Attorney, Agent, or Firm*—Weaver Austin Villeneuve & Sampson LLP; Emily M. Haliday

(57) ABSTRACT

The present invention provides a method of detecting nucleotide sequence differences between two nucleic acid samples. The method employs a comparative genomic hybridization (CGH) technique to analyze the sequence differences between the samples. This method permits the identification of small sequence differences (e.g., sequence divergence of 1% or less) in nucleic acid samples of high complexity (e.g., an entire genome).

11 Claims, 10 Drawing Sheets

U.S. PATENT DOCUMENTS

| | | | | | |
|---|---|---|---|---|---|
| 5,856,097 | A | * | 1/1999 | Pinkel et al. ............... | 435/6 |
| 5,965,362 | A | * | 10/1999 | Pinkel et al. ............... | 435/6 |
| 5,976,790 | A | * | 11/1999 | Pinkel et al. ............... | 435/6 |
| 6,100,030 | A | * | 8/2000 | McCasky Feazel et al. .... | 435/6 |
| 6,159,685 | A | * | 12/2000 | Pinkel et al. ............... | 435/6 |
| 6,335,167 | B1 | * | 1/2002 | Pinkel et al. ............... | 435/6 |
| 7,094,534 | B2 | | 8/2006 | Pinkel et al. | |
| 7,238,484 | B2 | | 7/2007 | Pinkel et al. | |
| 2003/0186250 | A1 | * | 10/2003 | Shah ............................. | 435/6 |
| 2005/0064476 | A1 | * | 3/2005 | Huang et al. ............... | 435/6 |
| 2005/0118634 | A1 | * | 6/2005 | Pinkel et al. ............... | 435/6 |

FOREIGN PATENT DOCUMENTS

| | | |
|---|---|---|
| CA | 2181543 | 9/2002 |
| EP | 0237362 B1 | 9/1987 |
| EP | 0326989 | 8/1989 |
| EP | 0430402 | 6/1991 |
| GB | 2019408 | 10/1979 |
| GB | 2215724 | 9/1989 |
| JP | 3645903 | 3/1993 |
| WO | WO 87/05027 | 8/1987 |
| WO | WO 90/05789 | 5/1990 |
| WO | WO/93/18186 | 9/1993 |
| WO | PCT/US2005/005131 | 2/2005 |

OTHER PUBLICATIONS

Office Action dated Jun. 247, 1995 issued in U.S. Appl. No. 08/223,905.
EP Search Report Dated May 15, 1993 from PCT/93/01775.
EP Search Report Dated Nov. 13, 2003, from EP Patent Application No. EP 01 20 0109.
EP Search Report Dated Sep. 11, 1999 from EP Patent Application No. EP 98 20 2403.
Angerer et al., "In Situ Hybridization to Cellular RNAs" Genetic Engineering: Principles and Methods, Setlow and Hollaender, Eds. 7, pp. 43-65, Plenum Press, New York (1985).
Ardeshir et al., "Structure of Amplified DNA in Different Syrian Hamster Cell Lines Resistant to N-(Phosphonacetyl)-L-Aspartate," Molecular and Cellular Biology 3(11), Nov. 1983, pp. 2076-2088.
Arnoldus et al., "Detection of the Philadelphia Chromosome in Interphase Nuclei (With 2 Color Plates)," Cytogenet. Cell Genet. 54, 1990, pp. 108-111.
Babu et al., "Tumor behavior in transitional cell carcinoma of the bladder in relation to chromosomal markers and histopathology," Cancer Res. 47:6800-6805, Dec. 1987.
Bar-Am et al., "Detection of Amplified DNA Sequences in Human Tumor Cell Lines by Fluorescence in situ Hybridization," Genes, Chromosomes & Cancer 4:314-320 (1992).
Barrios et al., "Constitutional del(3)(p14-p21) in a patient with bladder carcinoma," Cancer Genet. Cytogenet. 21(2):171-173 Abstract only, 1986.
Bayer et al., "The Use of Avidin-Biotin Complex as a Tool in Molecular Biology," Methods of Biochemical Analysis 26, pp. 1-45 (1980).
Becher et al., Cancer Research (1983) 43:5010-5016.
Benton et al., "Screening .lamda.gt Recombinant Clones by Hybridization to Single Plaques in situ," Science 196:180-182 (1977).
Bergerheim et al., "Deletion Mapping in Human Renal Cell Carcinoma," Cancer Res. 49:1390-1396 (Mar. 1989).
Bloomfield et al., "Nonrandom chormosome abnormalities in lymophoma," Cancer Research (1983) 43:2975-2984.
Bookstein et al., "Human Retinoblastoma Susceptibility Gene: Genomic Organization and Analysis of Heterozygous Intragenic Deletion Mutants," PNAS (USA) 85:2210-2214 (Apr. 1988).
Boyle, et al., "Differential Distribution of Long and Short Interspersed Element Sequences in the Mouse Genome: Chromosome Karyotyping by Fluorescence in situ Hybridization," Proc. Natl. Acad. Sci 87, pp. 7757-7761, Oct. 1990.
Boyle, et al., "Differential Distribution of Long and Short Interspersed Element Sequences in the Mouse Genome: Chromosome Karyotyping by Fluorescence in situ Hybridization," PNAS Sci. USA 87, 1990, pp. 7757-7761.
Brigati et al., "Detection of Viral Genomes in Cultured Cells and Paraffin-Embedded Tissue Sections Using Biotin-Labeled Hybridization Probes," Virology 126:32-50 (1983).
Brison et al., "General Method for Cloning Amplified DNA by Differential Screening With Genomic Probes," Molecular and Cellular Biology 2(5):578-587 (May 1982).
Britten et al., "Analysis of Repeating DNA Sequences by Reassociation," Methods of Enzymology 29:363-418 (1974).
Brock et al., "Quantitative in situ Hybridization Reveals Extent of Sequence Homology Between Related DNA Sequence in Drosphilia melanogaster," Chromosoma 83:159-168 (1981).
Broker et al., "Electron Microscopic Visualization of tRNA Genes with Ferritin-Avidin: Biotin Labels," Nucleic Acids Research 5(2):363-384 (1978).
Bufton et al., "A Highly Polymorphic Locus on Chromosome 16q Revealed by a Probe from a Chromosome-Specific Cosmid Library," Human Genetics 74:425-431 (1986).
Bufton et al., "Four Restriction Fragment Length Polymorphisms Revealed by Probes From a Single Cosmid Map to Human Chromosome 19," Am. J. Hum. Genet. 38:447-460 (1986).
Buongiorno-Nardelli et al., "Autoradiographic Detection of Molecular Hybrids between RNA and DNA in Tissue Sections," Nature 225:946-948 (Mar. 1970).
Burk et al., "Organization and Chromosomal Specificity of Autosomal Homologs of Human Y Chromosome Repeated DNA," Chromosoma 92:225-233 (1985).
Buroker et al., "Four Restriction Fragment Length Polymorphisms Revealed By Probes From a Single Cosmid Map to Human Chromosome 12q," Human Genetics 72:86-94 (1986).
Cannizzaro et al., "In Situ Hybridization and Translocation Breakpoint Mapping II. Two Unusual t(21;22) Translocations," Cytogenet. Cell Genet. 39, 1985, pp. 173-178.
Cantor et al., "The Behavior of Biological Macromolecules, Part III," Biophysical Chemistry, Freeman & Co. 1980, pp. 1183, 1226-1228.
Cassidy et al., "Deletion of chromosome 15(q11-13) in Prader-Labhart-Willi syndrom clinic population," Am. J. Med. Genet. 17:485-495, 1984.
Cherif et al., "Selection of cells with different chromosomal localizations of the amplified c-myc gene during in vivo and in vitro growth of the breast carcinoma cell line SW 613-S," Chromosoma 97:327-333, 1989.
Cohen et al., "Hereditary Renal-Cell Carcinoma Associated with a Chromosomal Translocation," N. Engl. J. Med. 301(11), Sep. 1979, pp. 592-595.
Colb et al., "A variable tandem repeat locus mapped to chromosome band 10q26 is amplified and rearranged in leukocyte DNAs of two cancer patients," Nucleic Acids Res. 14(20):7929-7937, 1986.
Collins et al., "Directional cloning of DNA fragments at a large distance from an initial probe: A circularization method," PNAS (USA), 81: 6812-6816 (Nov. 1984).
Connolly et al., "Chemical Synthesis of Oligonucleotides Containing a Free Sulphydryl Group and Subsequent Attachment of Thiol Specific Probes," Nucleic Acids Research 13(12), pp. 4485-4502 (1985).
Cote et al., "Quantitiation of in situ Hybridization of Ribosomal Ribonucleic Acids to Human Diploid Cells," Chromosoma 80, 1980, pp. 349-367.
Cox et al., "Detection of mRNAs in Sea Urchin Embryos by in Situ Hybridization Using Asymmetric RNA Probes," Developmental Biology 101, 1984, pp. 485-502.
Cremer et al., "Detection of Chromosome Aberrations in Metaphase and Interphase Tumor Cells by In Situ Hybridization Using Chromosome-specific Library Probes," Human Genetics 80:235-246 (1988).
Cremer et al., "Detection of Chromosome Aberrations in the Human Interphase Nucleus by Visualization of Specific Target DNAs with Radioactive and Non-Radioactive in situ Hybridization Techniques: Diagnosis of Trisomy 18 with Probe L1.84," Human Genetics 74, 1986, pp. 346-352.

Cremer et al., "Preparative Dual-Beam Sorting of the Human Y Chromosome and In Situ Hybridization of Cloned DNA Probes," Cytometry 5, 1984, pp. 572-579.

Cremer et al., "Rapid Interphase and Metaphase Assessment of Specific Chromosomal Changes in Neuroectodermal Tumor Cells by in Situ Hybridization with Chemically Modified DNA Probes," Exp. Cells Res. 176, 1988, pp. 199-220.

Cremer et al., "Rapid Metaphase and Interphase Detection of Radiation-Induced Chromosome Aberrations in Human Lymphocytes by Chromosomal Suppresion In Situ Hybridization," Cytometry 11:110-118 (1990).

Cuneo et al., "Multipotent stem cell involvement in megakaryoblastic leukemia: cytologic and cytogenetic evidence in 15 patients," Blood 74(5):1781-1790, Oct. 1989.

Davies, "The Application of DNA Recombinant Technology to the Analysis of the Human Genome and Genetic Disease," Human Genetics 58:351-357 (1981).

Dennis et al., "Cytogenetics of the Parthenogenetic Grasshopper Warramaba virgo and its Bisexual Relatives," Chromosoma 82:453-469 (1981).

Devilee et al., "Detection of Chromosome Aneuploidy in Interphase Nuclei from Human Primary Breast Tumors Using Chromosome-Specific Repetitive DNA Probes," Cancer Res. 48:5825-5830 (Oct. 1988).

Diaz et al., "Homozygous deletion of the alpha- and beta 1-interferon genes in human leukemia and derived cell lines," Proc. Nat. Acad. Sci. 85:5259-5263.

Diaz et al., "Homozygous deletion of the alpha- and beta 1-interferon genes in human leukemia and derived cell lines," Proc. Natl. Acad. Sci. 11(6), 1985, pp. 571-577.

Drmanac, R. et al., "Sequencing of Megabase Plus DNA by Hybridization: Theory of the Method," Genomics 4:114-128 (1989).

Durnam et al., "Detection of Species Specific Chromosomes in Somatic Cell Hybrids," Som. Cell. Molec. Genetics 11(6):571-577 (1985).

Dutrillaux et al., "Characterization of Chromosomal Anomalies in Human Breast Cancer—A Comparison of 30 Paradiploid Cases with Few Chromosome Changes," Cancer Genet. Cytogenet. 49, 1990, pp. 203-217.

Ehlen et al., "Loss of heterozygosity on chromosomal segments 3p, 6q, and 11p in human ovarian carcinomas," Oncogene 5:219-223, 1990.

Erikson et al., "Heterogeneity of Chromosome 22 Breakpoint in Philadelphia-positive (Ph+) Acute Lymphocytic Leukemia," PNAS, USA 83, Mar. 1986, pp. 1807-1811.

Flatov et al., "Differences in the localization of repeats of the alu family in certain chromosomes of peripheral blood cells of normal donors and bone marrow cells of patients with acute leukemia," Mol. Genet. Mikrobiol. Virusolog. 11:41-45, 1988.

Fisher et al., "Adhesive and Degradative Properties of Human Placental Cytotrophoblast Cells In Vitro," J. Cell Biol. 109(2):891-902 (1989).

Fisher et al., "Molecular Hybridization Under Conditions of High Stringency Permits Cloned DNA Segments Containing Reiterated DNA Sequences to be Assigned to Specific Chromosomal Locations," PNAS, USA 81:520-524 (Jan. 1984).

Flejter et al., "Recurring loss involving chromosomes 1, 3 and 22 in malignant mesothelioma: possible sites of tumor suppressor genes," Genes Chromosomes Cancer 1:138-154, 1989.

Friend et al., "A Human DNA Segment With Properties of the Gene that Predisposes to Retinoblastoma and Osteosarcoma," Nature 323:643-646 (Oct. 16, 1986).

Fuscoe et al., "An Efficient Method for Selecting Unique-Sequence Clones from DNA Libraries and Its Application to Fluorescent Staining of Human Chromosome 21 Using in situ Hybridization," Genomics 5:100-109 (1989).

Fuscoe et al., "Construction of Fifteen Human Chromosome-Specific DNA Libraries from Flow-Purified Chromosomes," Cytogenetic Cell Genetics 43:79-86 (1986).

Gall et al., "Formation and Detection of RNA-DNA Hybrid Molecules in Cytological Preparations," PNAS, USA 63:378-383 (1969).

Gall et al., "Nucleic Acid Hybridization in Biological Preparations," Methods in Enzymology 21:470-480 (1981).

Gerber et al., "Regional localization of a chromosom 3-specific DNA fragments by using a hybrid cell deletion mapping panel," Am. J. Hum. Genet. 43:442-451, 1988.

Gerhard et al., "Localization of a Unique Gene By Direct Hybridization in situ," PNAS 78:3755-3759 (1981).

Gibas et al., "A possible specific chromosome change in transitional cell carcinoma fo the bladder," Cancer Genet. Cytogenet. 19:229-238, Jan. 1986.

Gibas et al., "Chromosomal rearrangements in bladder cancer," Urology 23(3):3-9, Mar. 1984.

Gnatt et al., "Expression of alternatively terminated unusual human butyrylcholinesterase messenger RNA transcripts, mapping to chromosome 3q26-ter, in nervous system tumors," Cancer Res. 50:1983-1987, Apr. 1990.

Gray et al., "Flow Cytometric Detection of Chromosome Aberrations," (Abstract) Conference on Flow Cytometry in Cell Biology and Genetics, Clift Hotel, San Francisco, California, Jan. 15-17, 1985.

Gray et al., "Fluorenscence Hybridization to Human Chromosome 21 Using Probes From A Charon 21 A Library," Cytometry (Supp. 1) Abst. 19: p. 4 (1987).

Gray et al., "Molecular Cytogenetics, Diagnosis and Prognostic Assessment," Current Opinion in Biotechnology 3:623-631 (1992).

Grunstein et al., "Colony Hybridization: A Method for the Isolation of Cloned DNAs That Contain A Specific Gene," PNAS, USA 72(10):3961-3965 (Oct. 1975).

Haase et al., "Detection of Two Viral Genomes in Single Cells By Double-Label Hybridization in Situ and Color Microradiautography," Science 227, 1985, pp. 189-192.

Hainsworth et al., "Cytogenetic features of twenty six primary breast cancers," Cancer Genet. Cytogenet. (1991) 52:205-218.

Harper et al., "Localization of Single Copy DNA Sequences on G-Banded Human Chromosomes by in situ Hybridization," Chromosoma (Berl.) 83:431-439 (1981).

Henderson, "Cytological Hybridization to Mammalian Chromosomes," International Review of Cytology 76, pp. 1-46 (1982).

Herzenberg et al., "Fetal Cells in the Blood of Pregnant Women: Detection and Enrichment by Fluorescence-Activated Cell Sorting," PNAS, USA 76(3):1453-1455 (Mar. 1979).

Hill et al., "Cytogenetic analysis in human breast carcinoma. II. Seven cases in the triploid/tetraploid range investigated using direct preparations," Cancer Genet. Cytogenet. 24:45-62, 1987.

Hoeltke et al., "Multiple Nucleic Acid Labeling and Rainbow Detection," Analytical Biochemistry 207:24-31 (1992).

Holden et al., "Amplified Sequences from Chromosome 15, Including Centromeres, Nucleolar Organizer Regions, and Centromeric Heterochromatin, in Homogeneously Staining Regions in the Human Melanoma Cell Line MeWo," Cancer Genet. & Cytogenet. 14:131-146 (1985).

Hood et al., Molecular Biology of Eucaryotic Cells, W. A. Benjamin, Inc., Menlo Park, CA, pp. 47-51 (1975).

Houldsworth et al., "Comparative genomic hybridization: an overview," Am. J. Pathol. 145(6):1252-1260, Dec. 1994.

http://www.ndsu.nodak.edu/instruct/mcclean/plsc431/euk-karychrom/eukaryo3.-htm (accessed Mar. 10, 2006).

Jabs et al., "Characterization of a Cloned DNA Sequence that is Present at Centromeres of All Human Autosomes and the X Chromosome and Shows Polymorphic Variation," PNAS, USA 81:4884-4888 (Aug. 1984).

Jackson et al., "A double translocation culture t(5;15)t(9:11) with partial deletion of the short arm of chromosome 5," Cytogenet. Cell Genet. 15:400-401, 1975.

John et al., "RNA-DNA Hybrids at the Cytological Level," Nature 223:582-587 (Aug. 1969).

Joos et al., "Mapping and Chromosome Analysis: the Potential of Fluorescence In Situ Hybridization," Journal of Biotechnology 35:135-153 (1994).

Kallioniemi et al., "Comparative Genomic Hybridization for Molecular Cytogenetic Analysis of Solid Tumors," Science 258:818-821 (1992).

Kallioniemi et al., "Optimizing Comparative Genomic Hybridization for Analysis of DNA Sequence Copy Number Changes in Solid Tumors," Genes, Chromosomes, and Cancer 10:231-243 (1994).

Kao et al., "Assignment of the Structural Gene Coding for Albumin to Human Chromosome 4," Human Genetics 62:337-341 (1982).

Kievits et al., "Direct Nonradioactive In Situ Hybridization of Somatic Cell Hybrid DNA to Human Lymphocyte Chromosomes," Cytometry 11:105-109 (1990).

Klein et al., "Molecular and cytogenetic events in urologic tumors," Seminars in Urology 6(1):2-21, Feb. 1988.

Krumlauf et al., "Construction and Characterization of Genomic Libraries From Specific Human Chromosomes," PNAS 79:2971-2975 (1982).

Kuhlmann, Immuno Enzyme Techniques in Cytochemistry, Verlag Chemie, Weinheim, Basel (1984) (table of contents only).

KuNkel et al., "Organization and Heterogeneity of Sequences Within a Repeating Unit of Human Y Chromosome Deoxyribonucleic Acid," Biochem. 18:3343-3353 (1979).

Lakkala et al., "Comparison of DNA and karyotype aneuploidy in malignant lymphomas," Am. J. Clin. Pathol. 94:600-605, 1990.

Landegent et al., "2-Acetylaminofluorene-Modified Probes for the Indirect Hybridocytochemical detection of Specific Nucleic Acid Sequences," Exp. Cell Res., 153:61-72 (1984).

Landegent et al., "Chromosomal Localization of a Unique Gene by Non-autoradiographic in situ Hybridization," Nature 317:175-177 (Sep. 1985).

Landegent et al., "Fine Mapping of the Huntington Disease Linked D4S10 Locus By Non-radioactive in situ Hybridization," Human Genetics 73:354-357 (1986).

Landegent et al., "Use of Whole Cosmid Cloned Genomic Sequences for Chromosomal Localization of Non-Radioactive in situ Hybridization," Hum. Genet., 77:366-370 (1987).

Landegren et al., "DNA Diagnostics—Molecular Techniques and Automation," Science 242:229-237 (Oct. 1988).

Langer-Safer et al., "Immunological Method for Mapping Genes on Drosophila Polytene Chromosomes," PNAS, USA 79:4381-4385 (1982).

Langer-Safer et al., "Immunological Method for Mapping Genes on Drosphila Polytene Chromosomes," PNAS (USA) 79, 1982, pp. 4381-4385.

Lavialle et al., Anticancer Research (1989) 9:1265-1280.

Lawn et al., "The Isolation and Characterization of Linked .delta.- and .beta.-Globin Genes From a Cloned Library of Human DNA," Cell 15:1157-1174 (1978).

Lawrence et al., "Sensitive, High-Resolution Chromatin and Chromosome Mapping In Situ: Presence and Orientation of Two Closely Integrated Copies of EBV in a Lymphoma Line," Cell 52:51-61 (Jan. 1988).

Legrys et al., "Clinical Applications of DNA Probes in the Diagnosis of Genetic Diseases," CRC Crit. Rev. Clin. Lab. Sci., 25(4):255-274 (1987).

Lewin (editor), Genes, (2nd Edition John Wiley & Sons, Inc. 1984), pp. 298-299 and 464-465.

Lewin, "Genetic Probes Become Ever Shaper—Rapid Detection of Multiple-Pathogen Infections, Including Major Drug-Resistance Genes, May Be Possible Using A Newly Developed Technique," Science 221:4616:1167 (Sep. 1983).

Lewin, Genes, (2nd Ed., John Wiley & Sons, Inc. 1984) pp. 298-299 and pp. 464-465.

Lichter et al., "Delineation of Individual Human Chromosomes in Metaphase and Interphase Cells by In Situ Suppression Hybridization Using Recombinant DNA Libraries," Human Genetics 80:224-234 (1988).

Lichter et al., "Fluorescence in situ Hybridization with Alu and L1 Polymerase Chain Reaction Probes For Rapid Characterization Of Human Chromosomes In Hybrid Cell Lines," PNAS, USA 87, 1990, pp. 6634-6638.

Lichter et al., "High Resolution Mapping of Human Chromosome 11 by in Situ Hybridization with Cosmid Clones," Science 247, Jan. 5, 1990, pp. 64-69.

Lichter et al., "High Resolution Mapping of Human Chromosome 11 by in situ Hybridization with Cosmid Clones," Science 247:64-691 (Jan. 5, 1990).

Lichter et al., "Is Non-Isotopic in situ Hybridization Finally Coming of Age?" Nature 345:93-94 (May 1990).

Lichter et al., "Rapid Detection of Human Chromosome 21 Aberrations by in situ Hybridization," PNAS, USA 85:9664-9668 (Dec. 1988).

Linnenbach et al., "Structural alteration in the MYB protooncogene and deletion within the gene encoding alpha-type protein kinase C in human melanoma cell lines," Proc. Natl. Acad. Sci. 85:74-78, Jan. 1988.

Litt et al., "A Highly Polymorphic Locus in Human DNA Revealed by Cosmid-Derived Probes," PNAS, USA 82:6206-6210 (Sep. 1985).

Litt et al., "A Highly Polymorphic Locus in Human DNA Revealed by Probes From Cosmid 1-5 Maps to Chromosome 2q35-37," Am. J. Hum. Gent. 38:288-296 (1986).

Litt et al., "A Polymorphic Locus on the Long Arm of Chromosome 20 Defined by Two Probes From a Single Cosmid," Human Genetics 73:340-345 (1986).

LLNL, "Chromosome-Specific Human Gene Libraries," Energy & Tech. Review, Jul. 1985, pp. 82-83.

LLNL, "Fluorescent Labeling of Human Chromosomes with Recombinant DNA Probes," Energy & Tech. Review, Jul. 1985, pp. 84-85.

Au et al., "A General Method for Detecting Rearrangements in a Bacterial Genome," Proceedings of the National Academy of Sciences of the United States 86(14), 1989, pp. 5507-5511.

Lucas et al., "Rapid Translocation Analysis Using Fluorescence In Situ Hybridization: Applied to Long Term Biological Dosimetry," (UCRL 102265 Abstract) Radiation Research Meeting, New Orleans, Louisiana (Apr. 7-12, 1990).

Lundgren et al., "A squamous cell bladder carcinoma with karyotypic abnormalities reminiscent of transitional cell carcinoma," J. Urol. 142:374-376. May 1991.

Lysov et al., "Determination of the Nucleotide Sequence of DNA Using Hybridization with Oligonucleotides, A New Method," Doklady Biochemistry 303:436-438, translated from Doklady Akademii Nauk SSSR 303:1508-1511 (1988).

Malcolm et al., "Chromosomal Localization of a Single Copy Gene By in situ Hybridization-Human .beta. Globin Genes on the Short Arm of Chromosome 11," Ann. Hum. Genet. 45:134-141 (1981).

Mandahl et al., "Characteristic karyotypic anomalies identify subytpes of malignant fibrous histiocytoma," Genes Chromosomes Cancer 1(1):9-14, 1989.

Maniatis et al., "In Vitro Packagingg of Bacteriophage .lambda. DNA," Molecular Cloning: A Laboratory Manual, Cold Spring Harbor Laboratory, pp. 256-307 (1982).

Manuelidis et al., "Chromosomal and Nuclear Distribution of the Hindlll 1.9-kb Human DNA Repeat Segment," Chromosoma (Berl.) 91:28-38 (1984).

Manuelidis et al., "Different Central Nervous System Cell Types Display Distinct and Nonrandom Arrangements of Satellite DNA Sequences," PNAS (USA) 81:3123-3127 (May 1984).

Manuelidis, "Individual Interphase Chromosome Domains Revealed by in situ Hybridization," Hum. Genet. 71:288-293 (1985).

Mariani-Costantini et al., "Genomic alterations in human breat cancer: a Review," Tumori, 75:311-320, 1989.

Marmur, "A Procedure for the Isolation of Deoxyribonucleic Acid from Micro-organisms," J. Mol. Biol. 3:208-218 (1961).

Martsolf et al., "Familial transmission of Wolf syndrome resulting from specific deletion of 4p16 from t(4;8)(p16;p21) mat." Clin. Genet. 31:366-369, 1987.

Matthews, "Analytical strategies for the use of DNA probes," Anal. Biochem. 169:1-25, 1988.

McCormick, "The Polymerase Chain Reaction and Cancer Diagnosis," Cancer Cells 1(2):56-61 (Oct. 1989).

Miller et al., "Familial balanced insertional translocation of chromosome 7 leading to offspring with deletion and duplication of the inserted segment, 7p15-7p21," Am. J. Med. Genet. 4:323-332, 1979.

Montgomery et al., "Specific DNA Sequence Amplification in Human Neuroblastoma Cells," PNAS USA 80:5724-5728 (Sep. 1983).

Nederlof et al., "Detection of Chromosome Aberrations in Interphse Tumor Nuclei by Nonradioactive In Situ Hybridization," Cancer Genet. Cytogenet. 42:87-98 (1989).

Nederlof et al., "Fluorescence Ratio Measurements of Double-Labeled Probes for Multiple In Situ Hybridization by Digital Imaging Microscopy," Cytometry 13:839-845 (1992).

Nederlof et al., "Quantification of Inter- and Intra-Nuclear Variation of Fluorescence In Situ Hybridization Signals," Cytometry 13:831-838 (1992).

Nelson et al., "Genomic Mismatch Scanning: A New Approach to Genetic Linkage Mapping," Nature Genetics 4:11-18 (1993).

Nishida et al., "Nonrandom rearrangement of chromosome 14 at band q32.33 in human lymphoid malignancies with mature B-cell phenotype," Cancer Res. 49:1275-1281, Mar. 1989.

Olsen et al., "Isolation of Unique Sequence Human X Chromosomal Deoxyribonucleic Acid," Biochemistry 19:2419-2428 (1980).

Park et al., "Amplification, Overexpression, and Rearrangement of the erbB-2 Protooncogene in Primary Human Stomach Carcinomas," Cancer Res. 49, 1989, pp. 6605-6609.

Perucca et al., "Molecular genetics of human bladder carcinomas," Cancer Genet. Cytogenet. 49(2):143-156, Oct. 1990.

Phillips et al., "Multi-color Fluorescence In Situ Hybridization With Early Replicating DNA Libraries," Proceedings of the American Association for Cancer Research 35:A3450 Abstract (1994).

Pierce et al., "Analysis of a Dispersed Repetitive DNA Sequence in Isogenic Lines of Drosophila," Chromosoma 82:471-492 (1981).

Piker et al., "Cytogenetic findings in acute monocytic leukemia in a renal allograft recipient," Cancer Genet. Cytogenet. 20:101-107, 1986.

Pinkel et al., "Cytogenetic Analysis by In Situ Hybridization with Fluorescently Labeled Nucleic Acid Probes," Cold Spring Harbor Symposia on Quantitative Biology L1, 1986, pp. 151-157.

Pinkel et al., "Cytogenetic Analysis During Leukemia Therapy Using Fluorescence in situ Hybridization With Chromosome-Specific Nucleic Acid Probes," Am. J. Hum. Genet. (Supplement) 41(3):A34 (096;12.12) (Sep. 1987).

Pinkel et al., "Cytogenetic Analysis Using Quantitative, High-Sensitivity, Fluorescence Hybridization," PNAS (USA) 83:2934-2938 (May 1986).

Pinkel et al., "Cytogenetics Using Fluorescent Nucleic Acid Probes and Quantitative Microscopic Measurement," (UCRL 93269 Abstract) Analytical Cytology X Conference, Hilton Head Resort, Hilton Head Island, S.C. (Nov. 17-22, 1985).

Pinkel et al., "Detection of Structural and Numerical Abnormalities in Metaphase Spreads and Interphase Nuclei Using In Situ Hybridization," Cancer Genet. and Cytogenet. (UCRL 101043 Abstract) 41:236 (Oct. 1989).

Pinkel et al., "Detection of Structural Chromosome Aberrations in Metaphase Spreads and Interphase Nuclei by in situ Hybridization High Complexity Probes Which Stain Entire Human Chromosomes," Am. J. Hum. Genet. (Supplement) 43(3):A118 (Abstract 0471:11.5) (Sep. 1988).

Pinkel et al., "Detection of Translocations and Aneuploidy in Metaphase Spreads and Interphase Nuclei by In Situ Hybridization with Probes Which Stain Entire Human Chromosomes," (UCRL 101042 Abstract) 21.sup.st Oak Ridge Conference on Advanced Concepts in the Clinical Laboratory, (Apr. 13-14, 1989).

Pinkel et al., "Fluorescence In Situ Hybridization with Human Chromosome-Specific Libraries: Detection of Trisomy 21 and Translocations of Chromosome 4," PNAS (USA), 85:9138-9142 (Dec. 1988).

Pinkel et al., "Genetic Analysis by Quantitative Microscopy and Flow Cytometry Using Fluorescence In Situ Hybridization With Chromosome-Specific Nucleic Acid Probes," Am. J. Hum. Genet. (Supplement) 39(3):A129 (379)(Sep. 1986).

Pinkel et al., "Rapid Quantitative Cytogenic Analysis Using Fluorescently Labeled Nucleic Acid Probes," (UCRL 93553 Abstract), U.S.—Japan Joint Environmental Panel Conf., Research Triangle Park, N.C. (Oct. 21-23, 1985).

Pinkel et al., "Simplified Cytogenetics Using Biotin Labeled Nucleic Acid Probes and Quantitative Fluorescence Microscopy," Am. J. Hum. Genet. (Supplement) 37(4):A112 (328; 17.2) (Jul. 1985).

Pinkel, "Genome-wide analysis of DNA copy number array CGH" Department of Health and Human Services Public Health Service Grant Application, Nov. 12, 1997, pp. 1-73.

Porteus et al., "Human-Mouse Hybrids Carrying Fragments of Single Human Chromosomes Selected by Tumor Growth," Genomics 5, 1989, pp. 680-684.

Presti et al., "Molecular Genetic Alterations in Superficial and Locally Advanced Human Bladder Cancer," Cancer Research 51(19), Oct. 1991, pp. 5405-5409.

Rabin et al., "Mapping Minimally Reiterated Genes on Diploid Chromosomes by in situ Hybridization," Thesis, Dept. of Biochemistry, Univ. Ill. (1982).

Rabin et al., "Two Homeo Box Loci Mapped in Evolutionarily Related Mouse and Human Chromosomes," Nature 314:175-178 (1985).

Rappold et al., "Sex Chromosome Positions in Human Interphase Nuclei as Studied By In Situ Hybridization With Chromosome Specific DNA Probes," Human Genetics 67: 317-322 (1984).

Renz et al., "A Colorimetric Method for DNA Hybridization," Nucleic Acids Research 12(8):3435-44 (1984).

Renz, "Polynucleotide-Histone H1 Complexes as Probes for Blot Hybridization," EMBO Journal 2(6):817-822 (1983).

Richardson et al., "Biotin and Fluorescent Labeling of RNA Using T4 RNA Ligase," Nucleic Acids Research 11(18):6167-6184 (1983).

Ried et al., "Simultaneous Visualization of Seven Different DNA Probes by in situ Hybridization Using Combinatorial Fluorescence and Digital Imaging Microscopy," Proc. Natl. Acad. Sci. USA 89:1388-1392 (Feb. 1992).

Rivera et al., "Del (8)(q212q2200) De Novo in a boy without Langer-Giedion syndrome," J. Genet. Hum. 31(5):413-418, Dec. 1983.

Roelofs et al., "Gene Amplification in Human Cells May Involve Interchromosomal Transposition and Persistance of the Original DNA Region," The New Biologist 4(1):75-86 (Jan. 1992).

Ruddle, "A New Era in Mammalian Gene Mapping: Somatic Cell Genetics and Recombinant DNA Methodologies," Nature 294:115-120 (1981).

Sain-Ruf et al., "Proto-Oncogene Amplification and Homogeneously Staining Regions in Human Breast Carcinomas," Genes, Chromosomes & Cancer 2:18-26 (1990).

Sanchez et al., "Complex translocation in a boy with trichorhinophalangeal syndrome," J. Med. Genet. 22(4):314-6, Abstract Only for This Reference, Aug. 1985.

Sandberg, "Chromosome changes in bladder cancer: clinical and other correlations," Cancer Genet. Cytogenet. 19:163-175, 1986.

Scalenghe et al., "Microdissection and Cloning of DNA from a Specific Region of Drosophila melangogaster Polytene Chromosomes," Chromosoma (Berl.) 82:205-216 (1981).

Schardin et al., "Specific Staining of Human Chromsomes in Chinese Hamster X Man Hybrid Cell Lines Demonstrates Interphase Chromosome Territories," Hum. Genet. 71: 281-287 (1985).

Schmeckpeper et al., "Partial Purification and Characterization of DNA from the Human X Chromosome," PNAS (USA) 76(12):6525-6528 (Dec. 1979).

Sealey et al., "Removal of Repeated Sequences from Hybridisation Probes," Nucleic Acid Research 13(6):1905-1922 (1985).

Selypes et al., "A Noninvasive Method for Determination of the Sex and Karyotype of the Fetus From the Maternal Blood," Hum. Genet. 79:357-359 (1988).

Sen et al., "Specific gene amplification associated with consistent chromosomal abnormality in independently established multi-drug resistant chinese hamster ovary cells," Chromosoma 95:117-125, 1987.

Sidransky et al., "Identification of p53 gene mutations in bladder cancer and urine samples," Science 252:706-708, May 1991.

Siracusa et al., "Use of Repetitive DNA Sequences to Distinguish Mus musculus and Mus caroli Cells by in situ Hybridization," J. Embryol. Exp. Morph. 73:163-178 (1983).

Skolnick et al., "Simultaneous Analysis of Multiple Polymorphic Loci Using Amplified Sequence Polymorphisms (ASPs)" Genomics 2:273-279 (1988).

Smith et al., "Distinctive Chromosomal Structures are Formed Very Early in the Amplification of CAD Genes in Syrian Hamster Cells," Cell 63:1219-1227 (Dec. 21, 1990).

Smith et al., "The Synthesis of Oligonucleotides Containing an Aliphatic Amino Group at the 5' Terminus: Synthesis of Fluorescent DNA Primers for Use in DNA Sequence Analysis," Nucleic Acids Research 13:2399-2412 (1985).

Smith et al., "The Synthesis of Oligonucleotides Containing an Aliphatic Amino Group at the 5' Terminus: Synthesis of Fluorescent DNA Primers for Use in DNA Sequence Analysis," Nucleic Acids Research 13(7):2399-2412 (1985).

Snijders et al., Mapping segmental and sequence variations among laboratory mice using BAC array CGH, *Genome Research*, 2005 15:302-311.

Sondermeijer et al., "The Activity of Two Heat Shock Loci of *Drosophila hydrei* in Tissue Culture Cells and Salivary Gland Cells as Analyzed by in situ Hybridization of Complementary DNA," Chromosoma 72:281-291 (1979).

Southern et al., "Analyzing and Comparing Nucleic Acid Sequences by Hybridization to Arrays of Oligonucleotides: Evaluation Using Experimental Models," Genomics 13:1008-1017 (1992).

Sparkes et al., "Regional Assignment of Genes from Human Esterase D and Retinoblastoma to Chromosome Band 13q14," Science 208:1042-1044 (May 30, 1988).

Squire et al., "A detailed analysis of chromosomal changes in heritable and non-heritable retinoblastoma," Human Genetics 70:291-301, 1985.

Steinemann et al., "Multiple Sex Chromosomes in *Drosophila miranda*: A System to Study the Degeneration of a Chromosome," Chromosoma 86:59-76 (1982).

Stewart et al., "Cloned DNA Probes Regionally Mapped to Human Chromosome 21 and Their Use in Determining the Origin of Nondisjunction," Nucleic Acids Research 13(11):4125-4132 (1985).

Straume et al., "Chromosome Translocation of Low Radiation Doses Quantified Using Fluorescent DNA Probes," (UCRL 93837 Abstract), Radiation Research Society Meeting, Las Vegas, Nevada (Apr. 12-17, 1986).

Szabo et al., "Quantitative in situ Hybridization of Ribosomal RNA Species to Polytene Chromosomes of *Drosophila melanogaster*," J. Mol. Biol. 115:539-563 (1977).

Szabo et al., "What's New With Hybridization in situ?" TIBS 7(11):425-427 (Dec. 1982).

Tchen et al., "Chemically Modified Nucleic Acids as Immunodetectable Probes in Hybridization Experiments," PNAS 81:3466-3470 (1984).

Thompson et al., Thompson & Thompson: Genetics in Medicine, 5th ed., W. B. Saunders Co., Philadelphia, PA, pp. 38-39 (1991).

Tkachuk, D.C. et al., "Clinical Applications of Fluorescence in situ Hybridization," Gata 8(2):67-74 (1991).

Trask et al., "Detection of DNA Sequences in Nuclei in Suspension by In Situ Hybridization and Dual Beam Flow Cytometry," (UCRL 93372 Abstract) Analytical Cytology X Conference, Hilton Head Resort, Hilton Head Island, S.C. (Nov. 17-22, 1985).

Trask et al., "Early Dihyrofolate Reductase Gene Amplification Events in CHO Cells Usually Occur on the Same Chromosome Arm as the Original Locus," Genes & Development 3:1913-1925 (1989).

Trask et al., "The Proximity of DNA Sequences in Interphase Cell Nuclei is Correlated to Genomic Distance and Permits Ordering of Cosmids Spanning 250 Kilobase Pairs," Genomics 5:710-717 (1989).

Trask et al., Trends in Genetics (1991) 7(5):149-154.

Trent et al., "Report of the Committee on Structural Chromosome Changes in Neoplasia," Cytogenet. Cell Genet. 51:533-562 (1989).

Tsuda et al., "Correlation between long term survival in Breast Cancer patients and amplification of two putative oncogene-coamplification units: hst-1/int-2 and c-erB-2/ear1," Cancer Research (1989) 49:3104-3108.

Van Dilla et al., "Construction and Availability of Human Chromosome-Specific DNA Libraries From Flow Sorted Chromosomes: Status Report," Am. J. of Hum. Genetics 37:A179 (R Supplement) (Jul. 1985).

Vanni et al., "Cytogenetic investigation of 30 bladder carcinomas," Cancer Genet. Cytogenet. 30:35-42, 1988.

Wallace et al., "The Use of Synthetic Oligonucleotides as Hybridization Probes—II Hybridization of Oligonucleotides of Mixed Sequence to Rabbit .beta. Globin DNA," Nucleic Acids Research 9(4):879-894 (1981).

Weiss et al., "Organization and Evolution of the Class I Gene Family in the Major Histocompatibility Complex of the C57BL/10 Mouse," Nature 310:23:650-655 (Aug. 1984).

Willard et al., "Isolation and Characterization of a Major Tandem Repeat Family from the Human X Chromosome," Nucleic Acids Research 11(7):2017-2033 (1983).

Wilson et al., "Occurrence of holoprosencephaly in chromosome 13 locus disorders cannot be explained by duplication/deficiency of a single locus," Am. J. Med. Genet. Suppl. 2:65-72, Abstract Only for This Reference, 1986.

Wilson et al., "The phenotypic and cytogenetic spectrum of partial trisomy 9," Am. J. Med. Genet. 20(2):277-282 Abstract Only for This Reference, Feb. 1985.

Windle et al., "A Central Role for Chromosome Breakage in Gene Amplification, Deletion Formation, and Amplicon Integration," Genes & Development 5:160-174 (1991).

Wolman et al., "Genetic markers as prognositc indicators in breast cancer," Cancer 70(6):1765-1774, Sep. 1992.

Yokota et al., "Loss of heterozygosity on chromosomes 3, 13 and 17 in small-cell carcinoma and on chromosome 3 in adenocarcinoma of the lung," Proc. Natl. Acad. Sci. 84:9252-9256, Dec. 1987.

Yoshida et al., "Human HST1 (HSTF1) gene maps to chromosome band 11q13 and coamplifies with the INT2 gene in human cancer," Proc. Natl. Acad. Sci. 85:4861-4864, Jul. 1988.

Yunis et al., "Localization of Sequences Specifying Messenger RNA to Light-Staining G-Bands of Human Chromosomes," Chromosoma (Berl.) 61:335-344 (1977).

* cited by examiner

A

B

Telecentric Optical Design, 2 X Magnification

| | |
|---|---|
| First lens | 75 mm fl |
| Second lens | 150 mm fl |
| Corrected spectral range | 460 - 750 nm |
| Aperture | 32 mm max, NA ~ 0.2 |
| Object field | 18 mm dia (12.5 mm square array) |
| Image field | 36 mm dia (25 mm square CCD) |

Use of two 150 mm fl lenses  1 X Magnification, 36 mm dia object

A

B

A

B

DETECTION OF NUCLEIC ACID SEQUENCE DIFFERENCES BY COMPARATIVE GENOMIC HYBRIDIZATION

CROSS-REFERENCE TO RELATED APPLICATIONS

This application is a continuation-in-part of U.S. Ser. No. 11/017,493, filed on Dec. 17, 2004, which is a continuation of U.S. Ser. No. 09/644,140, filed on Aug. 22, 2000, which is a continuation of U.S. Ser. No. 08/903,095, filed on Jul. 30, 1997, now U.S. Pat. No. 6,159,685, which is a continuation of U.S. Ser. No. 08/468,629, filed on Jun. 6, 1995, now U.S. Pat. No. 5,721,098, which is a continuation of U.S. Ser. No. 08/166,147, filed on Dec. 14, 1993, now abandoned, which is a continuation of U.S. Ser. No. 07/969,948, filed on Oct. 30, 1992, now abandoned, which is a continuation-in-part of U.S. Ser. No. 07/846,659, filed on Mar. 4, 1992, now abandoned. This application also claims the benefit of U.S. provisional application Ser. No. 60/545,429, filed on Feb. 17, 2004. Each of the applications cited above is incorporated by reference in its entirety.

STATEMENT AS TO RIGHTS TO INVENTIONS MADE UNDER FEDERALLY SPONSORED RESEARCH AND DEVELOPMENT

This invention was made with government support under grant no. U01 CA84118, awarded by the National Institutes of Health. The Government may have certain rights in the invention.

FIELD OF THE INVENTION

The invention relates generally to methods for detecting nucleic acid sequence differences between nucleic acids in at least two samples, and in particular embodiments, to the detection of sequence differences between genomes.

BACKGROUND OF THE INVENTION

Comparative Genomic Hybridization (CGH) allows the comparison of at least two samples of nucleic acids based on simultaneous hybridization to a set of target nucleic acids. The target nucleic acids are typically immobilized, e.g., in metaphase or interphase chromosomes or, more conveniently, in a nucleic acid array. The sample nucleic acids are typically labeled, with a different label for each different sample. In one embodiment, array CGH typically involves the simultaneous hybridization of genomic DNA from two cell populations to an array of elements containing DNA sequences from different locations in the genome. The two genomic DNA samples are differentially labeled, and the ratio of the intensities of the hybridization to an array element is proportional to the relative copy number of sequences in the two genomes that bind to the element. Comparison of ratios among the elements allows detection of variations in relative DNA copy number among the different sequences on the array.

The degree of identity of sequence between two DNA fragments affects their ability to hybridize, so that hybridization of fragments with significantly different sequences can be strongly discriminated against by choosing appropriate hybridization conditions. For example arrays designed to detect specific base changes typically use oligonucleotides of about 20 nucleotides in length with a base change in the middle. This is about a 5% sequence difference and specific oligonucleotides need to be designed for each difference that it is desired to detect. Specifically designed arrays are used to detect many of these differences at the same time.

In the present invention, array CGH is employed to identify sequence differences between two nucleic acid samples. In particular, sequence differences between the two genomic DNAs on the order of 1 nucleotide every 100 bases, or even fewer, <1% sequence difference can be detected using a generic array made from large genomic (e.g., BAC) clones. Accordingly, one embodiment of the invention provides a rapid method of mapping the genomic constituents, such as genes that influence risk of disease. Current mapping procedures are very labor intensive, requiring individual analysis of each locus or development of specific arrays based on known sequence differences.

SUMMARY OF THE INVENTION

The invention provides a method of detecting one or more nucleotide sequence differences in nucleic acid sequences in a first sample relative to nucleic acid sequences in a second sample. The method entails labeling nucleic acids from each sample with a different label. The labeled nucleic acids from each sample are contacted with target nucleic acids. Generally, either the labeled nucleic acids or the target nucleic acids, or both, have had repetitive sequences, if initially present, blocked and/or removed. Preferably, the labeled nucleic acids from each sample are contacted with the target nucleic acids simultaneously. The intensities of the signals from the labeled nucleic acids hybridized to the target nucleic acids are compared to detect one or more nucleotide sequence differences between the samples.

In specific embodiments, the labeled nucleic acids from each sample are contacted with an array of target elements comprising the target nucleic acids. The intensities of the signals from the labeled nucleic acids hybridized to each target element are compared to detect one or more nucleotide sequence differences between the samples. Generally, the comparison entails determining the ratio of signal intensity of the labeled nucleic acids from said first and second samples to each target element. The ratio for one target element is then typically compared with the ratio for another target element. In the array-format version of the method, the sequence complexity of each target element can be greater than 20 bases and the sequence divergence between the samples can be less than about 10%. In preferred embodiments, the sequence complexity of each target element between about 50 kilobases to about 500 kilobases, and more preferably between about 75 kilobases and 300 kilobases. The sequence divergence between the samples is preferably about 5% or less, and more preferably about 1% or less In preferred embodiments, the target nucleic acids comprise DNA molecules, and in specific, preferred embodiments, genomic DNA molecules. Thus, for example, the plurality of target nucleic acids can comprise a plurality of different genomic DNA molecules, selected from different loci in a reference genome. In variations of this embodiment, the plurality of different genomic DNA molecules is selected from at least about 1000, at least about 5000, or at least about 10,000 different loci in the reference genome. The target nucleic acids can be derived from a nucleic acid library. In specific embodiments, the target nucleic acids are derived from YAC, BAC, P1, PAC, cosmid, cDNA clones or oligonucleotides. In specific embodiments, the array is a microarray comprising at least about 1000 target elements affixed to a 1 cm$^2$ region of substrate.

In preferred embodiments, the labeled nucleic acids comprise DNA molecules, and in specific, preferred embodiments, genomic DNA molecules. Alternatively, the labeled nucleic acids can comprise RNA molecules synthesized using genomic DNA as a template. The labeled nucleic acids can be derived from a nucleic acid library. In specific embodiments, the labeled nucleic acids are derived from YAC, BAC, P1, PAC, or cosmid clones. The samples can comprise nucleic acids derived from different species or the same species. In an example of the latter, the samples comprise nucleic acids from different strains of a species, such as, for example, different mouse strains. In preferred embodiments, the samples comprise nucleic acids from related individuals.

In an embodiment useful in mapping genes that influence a characteristic of interest, one sample comprises nucleic acids from a parental strain or species that is crossed with another strain or species to produce an F1 individual, and another sample comprises nucleic acids from an individual resulting from the backcross of the F1 individual with one of the parental strains or species. The results of the comparison of a backcross individual to one of the parental strains or species can be normalized by the results of a comparison of an F1 individual to one of the parental strains or species. In this embodiment, the detection of one or more nucleotide sequence differences can comprise determining whether the backcross individual is homozygous or heterozygous for the locus corresponding to each target element. Generally, the first sample is from an individual or plurality of individuals with a particular characteristic, and the second sample is from an individual or plurality of individuals that differ in that characteristic. In preferred variations of this embodiment, the characteristic comprises the risk of developing a disease, and one or more nucleotide sequence differences at a locus corresponding to a target element indicates that the locus may influence the risk of developing the disease, or that it may be linked to such a locus.

In another embodiment useful in identifying genes that influence a characteristic of interest, such as susceptibility to disease, the method entails detecting loss of heterozygosity at one or more loci in a first sample relative to a second sample. The samples preferably comprise nucleic acids derived from the same species. In preferred embodiments, the samples comprise nucleic acids from related individuals. For example, the first sample can comprise nucleic acids from a first F1 individual produced by crossing a parental strain with another (different) parental strain. In one embodiment, the second sample preferably comprises nucleic acids from a second F1 individual produced from this same cross. In another embodiment, the second sample comprises nucleic acids from a tumor from the first F1 individual. Generally, the first sample is from an individual or plurality of individuals with a particular characteristic, and the second sample is from an individual or plurality of individuals that differ in that characteristic. In preferred variations of this embodiment, the characteristic comprises the risk of developing a disease, and one or more nucleotide sequence differences at a locus corresponding to a target element indicates that the locus may influence the risk of developing the disease, or that it may be linked to such a locus.

Figure 1:
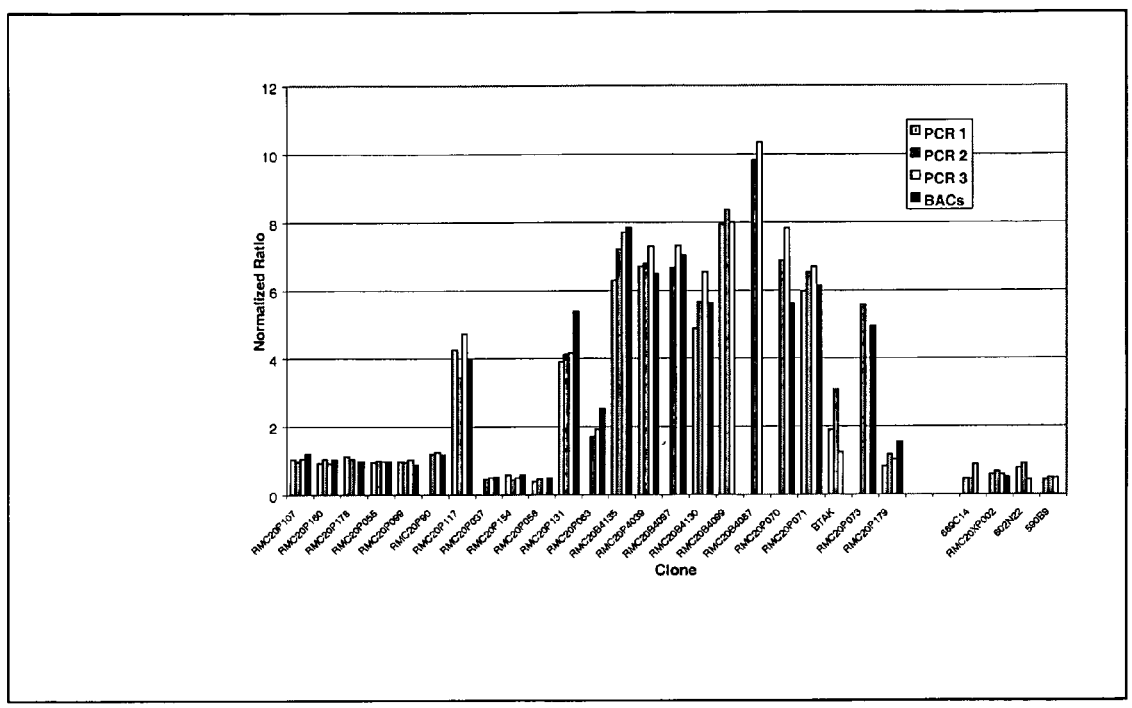
FIG. 1 shows the results of comparative genomic hybridization ("CGH") of DNA from the breast cancer cell line BT474 (labeled with FITC-dCTP) and normal female DNA (labeled with Cy3-dCTP) to an array containing target elements prepared from BAC clones containing chromosome 20 sequences using the methods of the invention. The ratio of the BT474 DNA: normal DNA hybridization signal (normalized ratio) is shown for amplification products prepared from BAC clones using ligation-mediated PCR (PCR1-3), as compared to historical data from an array of BAC DNA that was isolated conventionally. Three independently prepared amplification products were produced for most of the BAC clones that were amplified. These results demonstrate that ligation-mediated PCR produces an amplification product that is highly representative of (i.e., performs equivalently to) the BAC clone that serves as the template.

Panel A of each of the four figures shows the raw experimental data, and Panel B shows the result of analyzing the date using Hidden Markov models. The vertical axis is the log2 of the fluorescence ratio, and the horizontal axis represents the order of each clone on the array in genome. Vertical lines indicate boundaries of chromosomes. The statistical analysis divides the genome into two ratio levels and assigns each clone to one of the levels. The separation between the two levels in the Panel B represents the differences in the means of the ratios of clones assigned to the two levels.

FIGS. 7A and 7B shows the results for an F1 animal that has one copy of NIH sequence and one copy of Spretus sequence at all regions of the genome. The ratio is constant across the genome and the analysis finds that all clones are at one ratio level.

FIGS. 8A and 8B, 9A and 9B, and 10A and 10B show the results from different back cross mice. Now the ratios are not constant across the genome. Transitions between levels indicate the location in the genome where genome changes from having two copies of NIH sequences to one copy of a Spretus sequence and one copy of NIH sequence.

DETAILED DESCRIPTION

The present invention provides a method of detecting nucleotide sequence differences between two nucleic acid samples. The method employs a comparative genomic hybridization (CGH) technique to analyze the sequence differences between the samples. This method permits the identification of small sequence differences (e.g., sequence divergence of 1% or less) in nucleic acid samples of high complexity (e.g., an entire genome). Thus, the genomes of two closely related organisms can be compared to identify sequence differences that may account, at least in part, for differences in a characteristic of interest. For example, the genome of a mouse strain that is susceptible to a particular disease can be compared with that of a non-susceptible strain to identify candidate disease genes.

The method of the invention entails labeling nucleic acids from each sample with a different label and contacting the labeled nucleic acids from each sample with target nucleic acids. Generally, either the labeled nucleic acids or the target nucleic acids, or both, have had repetitive sequences, if initially present, blocked and/or removed. The intensities of the signals from labeled nucleic acids hybridized to each target element are compared to detect one or more nucleotide sequence differences between the samples.

In a preferred embodiments, the method is carried out by hybridizing the labeled nucleic acids to a nucleic acid array (termed "array CGH"), preferably a microarray. Preferably, the sequence complexity of each target element in the array is greater than 20 bases, and the sequence divergence between the samples is less than about 10%.

DEFINITIONS

The term "array" refers to a collection of elements, wherein each element is uniquely identifiable. For example, the term can refer to a substrate bearing an arrangement of elements, such that each element has a physical location on the surface of the substrate that is distinct from the location of every other element. In such an array, each element can be identifiable simply by virtue of its location. Typical arrays of this type include elements arranged linearly or in a two-dimensional matrix, although the term "array" encompasses any configuration of elements and includes elements arranged on nonplanar, as well as planar, surfaces. Non-planar arrays can be made, for example, by arranging beads, pins, or fibers to form an array. The term "array" also encompasses collections of elements that do not have a fixed relationship to one another. For example, a collection of beads in which each bead has an identifying characteristic can constitute an array.

The elements of an array are termed "target elements."

As used herein with reference to target elements, the term "distinct location" means that each element is physically separated from every other target element such that a signal (e.g., a fluorescent signal) from a labeled molecule bound to target element can be uniquely attributed to binding at that target element.

A "microarry" is an array in which the density of the target elements on the substrate surface is at least about $100/cm^2$.

The term "nucleic acid" refers to a deoxyribonucleotide or ribonucleotide polymer in either single- or double-stranded form, and unless otherwise limited, encompasses known analogs of natural nucleotides that can function in a similar manner to naturally occurring nucleotides.

A nucleic acid whose sequences are to be included in a single target element in a nucleic acid array is termed a "starting nucleic acid."

As used herein, a "nucleic acid product" is representative of the starting nucleic acid.

A nucleic acid product is said to be "representative" of a starting nucleic acid if the hybridization signal observed from the nucleic acid product is sufficiently similar to that observed from the starting nucleic acid that the nucleic acid product can be substituted for the starting nucleic acid in a hybridization assay. In other words, a representative nucleic acid product performs essentially equivalently to the starting nucleic acid in a hybridization assay of interest.

An array of nucleic acids is said to be "representative" of a collection of starting nucleic acids if the nucleic acids present in each target element are representative of the corresponding starting nucleic acid.

A nucleic acid is "double-stranded" if it contains two nucleic acid strands joined by hydrogen bonding. The nucleic acid strands need not be coextensive (i.e, a double-stranded nucleic acid need not be double-stranded along the entire length of both strands).

A "nucleic acid library" is a collection of nucleic acids derived, directly or indirectly, from a biological sample. Typical nucleic acid libraries include cloning vectors containing inserts corresponding to nucleic acid sequences in a biological sample; however, the term "nucleic acid library" also includes collections of nucleic acids that are not present in cloning vectors, such as, for example, genomic DNA, cDNA synthesized from mRNA, or nucleic acids amplified from a sample.

Nucleic acids that are the subject of CGH analysis to identify sequence differences are termed "sample nucleic acids."

"Sample nucleic acids" are analyzed by hybridizing them to "target nucleic acids."

As used herein, the term "genomic DNA" refers to DNA having genomic DNA sequences and includes, for example, DNA prepared by purifying or amplifying genomic DNA, as well as cloned genomic DNA.

The term "reference genome" is used herein to refer to a collection of genomic DNA molecules. The reference genome can include all or a portion of the genomic DNA sequences of an organism.

The term "adapter" is used herein to refer to a double-stranded nucleic acid that can be ligated to the end of a nucleic acid fragment to facilitate ligation-mediated amplification. Adapters are usually (but not necessarily) oligonucleotides of less than 100 bases in length.

"5' or 3' extensions" are single-stranded extensions at either end (or both ends) of an otherwise double-stranded nucleic acid. Typically, such extensions are produced upon digestion with a restriction endonuclease, but the invention is not limited to 5' or 3' extensions produced in this manner. Such extensions are said to be "common" if they share sufficient sequence homology to hybridize to a given oligonucleotide. For convenience, the method of the invention generally employs nucleic acid fragments that have 5' extensions that share the identical sequence.

As applied to nucleotide sequences, the term "complexity" is used herein according to standard meaning of this term as established by Britten et al. (1974) Methods of Enzymol. 29:363. See also, Cantor and Schimmel Biophysical Chemistry: Part III at 1228-1230 for a further explanation of nucleic acid complexity.

The term "sequence divergence" refers to the percentage difference between two nucleotide sequences or two collections of nucleotide sequences.

As used herein, the term "substantially complementary" describes sequences that are sufficiently complementary to one another to allow for specific hybridization under appropriately stringent hybridization conditions. "Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridizing conditions allows sequence mismatches to be tolerated.

A sample is said to be "derived from" an individual, regardless of whether it is obtained directly or indirectly from the individual. Thus, for example, one or more cells can be removed from an individual and subjected to cell culture, and the cultured cells can subsequently employed in the methods of the invention. As described herein, the cultured cells are still "derived from" the individual, despite the intervening culture step.

Comparative Genomic Hybridization—In General

The method of the invention employs Comparative Genomic Hybridization (CGH) to detect variations in the sequences of nucleic acids. CGH is widely used to detect variations in the nucleic acid sequence copy number between samples of nucleic acids, such as two genomes.

CGH has also been termed Copy Ratio Reverse Cytogenetics (CRRC), competition hybridization and quantitative in situ ratio karyotyping (QUIRK). Further, in the embodiment wherein fluorochromes are used as labels, it has been termed competition FISH (fluorescence in situ hybridization). CGH specifically provides methods whereby amplifications, duplications and/or deletions can be identified in an immediate overview of a genome. This technique is described in detail in U.S. Pat. No. 5,856,097, issued to Pinkel et al. on Jan. 5, 1999 and U.S. Pat. No. 6,159,685, issued to Pinkel et al. on Dec. 12, 2000.

CGH provides methods for determining variations in the copy number of different elements in a mixture of nucleic acid sequences (for example, genomic DNA isolated from a tumor) as a function of the location of those sequences in the genome of a reference organism (for example, the genome of a normal cell from the same species). The methods comprise the use of in situ hybridization of the nucleic acid sequence mixture to a chromosome spread of the reference organism, and measuring the intensity of the hybridization at different locations along the target chromosomes.

It is important that signals from repetitive sequences, if present, do not dominate the signal from the subject nucleic acid pool, and that they be removed from the pool or that their signals be suppressed as necessary. It is preferred to exclude sequences from the hybridization or block sequences in the hybridization mixture that could bind to multiple clearly separated positions on the chromosomes, for example, sites that are on different chromosomes, or that are on the same chromosome but are well-separated. In many applications of CGH, it is the high copy repetitive sequences, such as Alu, Kpn, Lines, and alpha-satellites among others, that are removed from the labeled subject nucleic acid and/or which are blocked and/or the binding sites therefore are blocked. Described herein are methods to remove and/or block those repetitive signals. It should be noted that nucleic acid sequences in the labeled nucleic acid that bind to single copy loci are substantially retained in the hybridization mixture of labeled subject nucleic acids, and such single copy sequences as well as their binding sites in the reference chromosome spread remain substantially unblocked relative to the repetitive sequences that bind to multiple loci (that is, loci that are visually distinguishable) both before and during the hybridization.

CGH provides the means to identify previously unknown regions of amplification and deletion. For example, one embodiment of CGH provides an efficient method that gives an immediate overview of a genome identifying all regions that are amplified greater than about five-fold to ten-fold as well as at least large deletions. More sensitive embodiments that can identify smaller amplifications and deletions are also feasible.

Nanogram quantities of the subject nucleic acids can be employed for CGH. Paraffin embedded tumor sections can be used as well as fresh or frozen material. Snap frozen material from normal and malignant tissue are preferred for mRNA isolation.

Standard procedures can be used to isolate the required nucleic acid from the subject cells. However, if the nucleic acid, for example, DNA or mRNA, is to be extracted from a low number of cells (as from a particular tumor subregion) or from a single cell, it is desirable to amplify that nucleic acid, by a polymerase chain reaction (PCR) procedure or by a non-polymerase chain reaction (non-PCR) procedure. PCR and preferred PCR procedures are described infra. Exemplary non-PCR procedures include the ligase chain reaction (LCR) and linear amplification by use of appropriate primers and their extension (random priming).

In one embodiment of CGH, a subject nucleic acid, in this case, human genomic DNA, is labeled differently from another subject nucleic acid, and amplifications and/or deletions are indicated by a change in ratio between the different signals, rather than just a change in signal intensity.

CGH can involve the hybridizations of tumor cell line DNA to normal human metaphase spreads. However, there are many possible permutations and combinations of pair-wise and multiple hybridizations of different nucleic acids from different genomes.

For example, CGH could be used to hybridize labeled DNA from a tumor cell line to metaphase spreads of that same cell line to estimate the level and pattern of amplification in each cell line, comparing those results to hybridizations of said tumor cell line DNA to a normal human metaphase spread. Alternatively, labeled tumor cell line DNA and differently labeled human genomic DNA could be simultaneously hybridized to a metaphase spread of a tumor cell line. Further, DNA from a primary tumor and that from its metastasis could be differently labeled and hybridized in a CGH method to a normal human metaphase or to a related tumor cell line metaphase. Those are just some of the many examples of CGH.

It will be clear to anyone skilled in the art that CGH is not limited to studying genomes of cancer cells or to the results of hybridizing abnormal genomes to normal genomes. CGH permits the comparison of nucleic acid sequence copy frequencies of any two or more genomes, even genomes of different species if their nucleic acid sequences are sufficiently complementary to allow for meaningful interpretation. It should be noted regarding interspecies comparisons that the information obtained by CGH includes not only an assessment of relative copy number but also that of sequence divergence.

It will also be clear to those skilled in the art that hybridization with nucleic acid other than chromosomal DNA, such as messenger RNA (mRNA) or complementary DNA (c-DNA) of subject cells can be used to determine the location and level of expression of genes in those cells. Conventional methodology is used to extract mRNA from a cell or cell population, and to synthesize in vitro c-DNA by reverse transcription.

CGH does not require the preparation of condensed chromosomes, for example, metaphase, prophase or other condensed chromosomal states, of the subject genomes. Thus, genomes from which metaphase, prophase or otherwise condensed chromosomal spreads are difficult, time-consuming or not possible to prepare at least in good quality, for example, genomes of tumor cells or fetal cells, can be studied by CGH.

In CGH, labeled subject nucleic acids, for example, labeled tumor DNA, can be hybridized to a reference genome, for example, a normal human metaphase spread, under conditions in which the signal from amplified, duplicated and/or deleted nucleic acid sequences from the labeled nucleic acid can be visualized with good contrast. Such visualization is accomplished by suppressing the hybridization of repetitive sequences that bind to multiple loci including the high copy interspersed and clustered repetitive sequences, such as, Alu, Kpn, Lines, alpha-satellites among others, using unlabeled total human genomic nucleic acid, preferably DNA, and/or the repeat-enriched (Cot-1) fraction of genomic DNA, and/or by removing such repetitive sequences from the hybridization mixture. In providing the detection sensitivity required, the extent of suppression of the hybridization of repetitive sequences and/or removal thereof can be adjusted to the extent necessary to provide adequate contrast to detect the differences in copy number being sought; for example, subtler copy number changes may require the suppression or removal of lower level repetitive sequences.

When combining more than one labeled nucleic acid in a hybridization mixture, the relative concentrations and/or labeling densities may be adjusted for various purposes. For example, when using visual observation or photography of the results, the individual color intensities need to be adjusted for optimum observability of changes in their relative intensities. Adjustments can also be made by selecting appropriate detection reagents (avidin, antibodies and the like), or by the design of the microscope filters among other parameters. When using quantitative image analysis, mathematical normalization can be used to compensate for general differences in the staining intensities of different colors.

The kinetics of the CGH hybridizations are complicated. Since the subject nucleic acids are frequently double stranded, complementary sequences will reassociate in the hybridiztion mix as well as hybridizing to the target.

Such reassociation may result in a more rapid decrease in concentration of the high copy sequences than the low copy ones, thereby making the signal intensity variations on the reference chromosomes less pronounced than the copy differences in the original subject DNAs. In addition, non-specific binding of the labeled subject DNAs to the slide, coverslip, etc. may generally reduce the concentration of that labeled subject nucleic acid during the hybridization. Those skilled in the art will recognize numerous methods of optimizing the quantitative aspects of CGH, such as, mathematical correction of digital images, supplying freshly denatured subject DNA during the hybridization, and adding unlabeled genomic DNA in excess to dominate the reassociation rates.

The resolution of CGH using metaphase chromosomes as the target is currently at a level that can be seen through a light microscope, as is traditional cytogenetic staining. Thus, if a small sequence in a subject nucleic acid is amplified, to be seen as a signal in a subject genome, it must be amplified enough times for its signal to be able to be visualized under a light microscope. On the other hand, if a large section of a chromosome is present at increased frequency in a subject nucleic acid, the signal from that region would show up in the reference genome at a much lower level of amplification.

The term "labeled" is herein used to indicate that there is some method to visualize nucleic acid fragments that are bound to the target, whether or not the fragments directly carry some modified constituent. A section infra entitled "Labeling the Nucleic Acid Fragments of the Subject Nucleic Acids" describes various means of directly labeling the probe and other labeling means by which the bound probe can be detected.

A base sequence at any point in the genome can be classified as either "single-copy" or "repetitive". For practical purposes the sequence needs to be long enough so that a complementary probe sequence can form a stable hybrid with the target sequence under the hybridization conditions being used. Such a length is typically in the range of several tens to hundreds of nucleotides.

A "single-copy sequence" is that wherein only one copy of the target nucleic acid sequence is present in the haploid genome. "Single-copy sequences" are also known in the art as "unique sequences". A probe complementary to a single-copy sequence has one binding site in haploid genome. A "repetitive sequence" is that wherein there is more than one copy of the same target nucleic acid sequence in the genome. Each copy of a repetitive sequence need not be identical to all the others. The important feature is that the sequence be sufficiently similar to the other members of the family of repetitive sequences such that under the hybridization conditions being used, the same fragment of probe nucleic acid is capable of forming stable hybrids with each copy.

Herein, the terms repetitive sequences, repeated sequences and repeats are used interchangeably.

The phrase "metaphase chromosomes" is herein defined to encompass the concept of "condensed chromosomes" and is defined to mean not only chromosomes condensed in the prophase or metaphase stage of mitosis but any condensed chromosomes, for example, those condensed by premature chromosome condensation or at any stage in the cell cycle wherein the chromosome can be visualized as an individual entity. It is preferred that the chromosomes in the reference genome be as long as possible but condensed sufficiently to be visualized individually.

The following abbreviations are used herein:

Abbreviations

AAF—N-acetoxy-N-2-acetyl-aminofluorene
ATCC-American Type Culture Collection
BN-bicarbonate buffer with NP-40
BRL-Bethesda Research Laboratories
bp-base pair
CCD-charge coupled device
CGH-Comparative Genomic Hybridization
Chr.-chromosomal
CML-chronic myelogenous leukemia
CRRC-Copy Ratio Reverse Cytogenetics
DAPI-4,6-diamidino-2-phenylindole
dATP-deoxyadenosine triphosphate
DCS-as in fluorescein-avidin DCS (a commercially available cell sorter grade of fluorescein Avidin D)
dCTP-deoxycytosine triphosphate
dGTP-deoxyguanosine triphosphate DI-DNA index
DM-double minute chromosome
dNTP-deoxynucleotide triphosphate
dTTP-deoxythymiidine triphosphate
dUTP-deoxyuridine triphosphate
EDTA-ethylenediaminetetraacetate
E/P-estrogen/progesterone
FISH-fluorescence in situ hybridization
FACS-fluorescence-activated cell sorting
FITC-fluorescein isothiocyanate
HPLC-high performance liquid chromatography
HSR-homogeneously staining region
ISCN-International System for Cytogenetic Nomenclature
IB-isolation buffer
kb-kilobase
kDa-kilodalton
LOH-loss of heterozygosity M.-mus
Mb-megabase
met.-metastasis
min-minute
ml-milliliter
mM-milliMole
mm-millimeter
ng-nanogram
NIGMS-National Institute of General Medical Sciences
NP-40-non-ionic detergent commercially available from Sigma as Nonidet P-40 (St. Louis, Mo.)
PBS-phosphate-buffered saline
PCR-polymerase chain reaction
PHA-phytohemagglutinin
PI-propidium iodide
Pl.-pleural
PMSF-phenylmethylsulfonyl fluoride
PN buffer-mixture of 0. 1M $NaH_2PO_4$ and 0.1M $Na_2HPO_4$, pH 8; 0.1% NP-40
PNM buffer-Pn buffer plus 5% nonfat dry milk (centrifuged); 0.02% Na azide
QUIRK-quantitative in situ ratio karyotyping
Rb-1-retinoblastoma tumor suppressor gene
RFLP-restriction fragment length polymorphism
RPM-revolutions per minute
SD-Standard Deviation
SDS-sodium dodecyl sulfate
SSC-0.15M NaCl/0.015M Na citrate, pH 7
Td-doubling time
μg-microgram
μl-microliter
μm-micrometer
μM-micromole
VNTR-variable number tandem repeat Resolution of differences in copy number can be improved by the use of image analysis and by averaging the results from hybridizations of a subject nucleic acid to multiple condensed chromosome spreads. Using such methods, the background signal (noise) can be differentiated from actual nucleic acid sequence copy number differences.

Image Analysis

An image analysis system, preferably computer-assisted, can be used to enhance and/or accurately quantify the intensity differences between and/or among the signals from a hybridization and the background staining differences for more accurate and easier interpretation of results. Image analysis and methods to measure intensity are described, for example, in Hiraoka et al., Science, 238: 36-41 (1987) and Aikens et al., Meth. Cell Biol., 29: 291-313 (1989). In such an image analysis system, it is preferred to use a high quality CCD camera whose intensity response is known to be linear over a wide range of intensities.

The components of a particular, exemplary quantitative image processing system (QUIPS) include a computer-assisted image analysis system with a filterwheel that is used so that the images from the signals and counterstaining of the DNA are superimposed on one image. Pseudocolors, that is, colors that are not exactly spectrally converted, can be displayed. Contrast stretching can be used, wherein the differences between the intensity levels of the signals and background staining differences are enhanced by adjusting controls of the image analysis system. Thresholding can also be used wherein the background staining can be assigned a value close to zero so it would barely appear in the processed image from such a system. Similarly, computer analysis permits subtraction of background, smoothing of fluctuations in the signals, accurate intensity and ratio calculations and the ability to average signals on chromosomes in multiple spreads.

Absolute Copy Numbers

Hybridization of the subject DNAs to the reference chromosomes gives information on relative copy numbers of sequences. Some additional normalization is required to obtain absolute copy number information. One convenient method to do this is to hybridize a probe, for example a cosmid specific to some single locus in the normal haploid genome, to the interphase nuclei of the subject cell or cell population(s) (or those of an equivalent cell or representative cells therefrom, respectively). Counting the hybridization signals in a representative population of such nuclei gives the absolute sequence copy number at that location. Given that information at one locus, the intensity (ratio) information from the hybridization of the subject DNA(s) to the reference condensed chromosomes gives the absolute copy number over the rest of the genome. In practice, use of more than one reference locus may be desirable. In this case, the best fit of the intensity (ratio) data through the reference loci would give a more accurate determination of absolute sequence copy number over the rest of the genome.

Thus, CGH methods combined with other well-known methods in the art can provide information on the absolute copy numbers of substantially all RNA or DNA sequences in subject cell(s) or cell population(s) as a function of the location of those sequences in a reference genome. For example, one or more chromosome-specific repeat sequence or high complexity painting probes can be hybridized independently to the interphase nuclei of cells representative of the genomic constitution of the subject cell(s) or cell population(s). Whole chromosome painting probes are now available for all the human chromosomes [Collins et al., Genomics, 11: 997-1006 (1991)]. Specific repeat-sequence probes are also available [Trask et al., Hum. Genet., 78: 251 (1988) and references cited therein; and commercially available from Oncor (Gaithersburg, Md., USA)]. Hybridization with one or more of such probes indicates the absolute copy numbers of the sequences to which the probes bind.

For such interphase analysis, painting probes with a complexity of from about 35 kb to about 200 kb, are preferred; probes from about 35 kb to about 100 kb are further preferred; and still more preferred are probes having a complexity of from about 35 kb to 40 kb, for example, a cosmid probe. Exemplary of such locus-specific painting probes are any cosmid, yeast artificial chromosomes (YACs), bacterial artificial chromosomes (BACs), and/or p1 phage probes as appropriate, preferably to the arms of a selected chromosome.

Such cosmid probes, for example, are commercially available from Clontech [South San Francisco, Calif. (USA)] which supplies cosmid libraries for all the human chromosomes. Another example of a cosmid probe that could be used in such methods would be a 3p cosmid probe called cC13-787 obtained from Yusuke Nakamura, M. D., Ph.D. [Division of Biochemistry, Cancer Institute, Toshima, Tokyo, 170, Japan]. Its isolation and mapping to 3p21.2-p21.1 is described in Yamakawa et al., Genomics, 9(3): 536-543 (1991). Another example would be a 3q cosmid probe named J14R1A12 obtained from Wen-Lin Kuo [Biomedical Department, P.O. Box 5507 (L-452), Lawrence Livermore National Laboratory Livermore, Calif. 94550 (USA)]. For interphase analysis, preferred repeat sequence probes are centromeric-specific and/or peri-centromeric-specific repeat sequence probes. Such a centromeric-probe is, for example, the chromosome 17 peri-centromeric repeat probe (cosmid ck17.10) and the alpha satellite repeat probe for the centromeric region of chromosome 8. A variety of repeat sequence probes are commercially available from Oncor [Gaithersburg, Md. (USA)]. However, the locus-specific painting probes are preferred over the repeat sequence probes determine absolute copy numbers of nucleic acid sequences.

Further, when the subject nucleic acid sequences are DNA, the reference copy numbers can be determined by Southern analysis. When the subject nucleic acid sequences are RNA, the reference copy numbers can be determined by Northern analysis.

Those reference copy numbers or reference frequencies provide a standard by which substantially all the RNA or DNA sequences in the subject cell(s) or cell population(s) can be determined. CGH methods are used to determine the relative copy numbers of the rest of the sequences. However, absolute copy numbers require a standard against which the results of CGH can be determined. Otherwise the CGH procedures would have to be highly standardized and quantified to see differences in the absolute copy numbers of sequences in a genome, for example, haploidy, triploidy, octaploidy, wherein there are 1, 3 and 8 copies of each of the chromosomes, respectively.

PCR and Microdissection

The mechanics of PCR are explained in Saiki et al., Science, 230: 1350 (1985) and U.S. Pat. Nos. 4,683,195, 4,683,202 (both issued Jul. 18, 1987) and U.S. Pat. No. 4,800,159 (issued Jan. 24, 1989).] PCR offers a rapid, sensitive and versatile cell-free molecular cloning system in which only minute amounts of starting material are required.

A preferred PCR method to amplify the subject nucleic acids for testing by CGH is a PCR adapter-linker amplification [Saunders et al., Nuc. Acids Res., 17 9027 (1990); Johnson, Genomics, 6: 243 (1990) and PCT 90/00434 (published Aug. 9, 1990).] The labeled subject nucleic acid could be produced by such a adapter-linker PCR method from a few hundred cells; for example, wherein the subject nucleic acid is tumor DNA, the source DNA could be a few hundred tumor cells. Such a method could provide a means to analyse by CGH clonal sub-populations in a tumor.

Another preferred PCR method is a method employing a mixture of primers described in Meltzer et al., "Rapid Generation of Region Specific Probes by Chromosome Microdissection and their Application: A Novel Approach to Identify Cryptic Chromosomal Rearrangements," Nature—Genetics, 1(1): 24-28 (April 1992). Microdissection of sites in the reference metaphase spread that produce signals of interest in CGH, would permit PCR amplification of nucleic acid sequences bound at such sites. The amplified nucleic acid could then be easily recovered and used to probe available libraries, as for example, cosmid libraries, so that the amplified sequences could be more rapidly identified.

High copy repetitive sequences can be suppressed in amplifying the subject nucleic acid by PCR. The PCR primers used for such a procedure are complementary to the ends of the repetitive sequences. Thus, upon proper orientation, amplification of the sequences flanked by the repeats occurs. One can further suppress production of repetitive sequences in such a PCR procedure by first hybridizing complementary sequences to said repetitive sequences wherein said complementary sequences have extended non-complementary flanking ends or are terminated in nucleotides which do not permit extension by the polymerase.

The non-complementary ends of the blocking sequences prevent the blocking sequences from acting as a PCR primer during the PCR process. Primers directed against the Alu and L1 repetitive DNA families have allowed the selective amplification of human sequences by interspersed repetitive sequence PCR (IRS-PCR) [Nelson et al., PNAS, 86: 6686 (1989); Ledbetter et al., Genomics, 6: 475 (1990)].

Archived Material

An important aspect of this invention is that nucleic acids from archived tissue specimens, for example, paraffin-embedded or formalin-fixed pathology specimens, can be tested by the methods of CGH. Said nucleic acid cannot, of course, be prepared into chromosome spreads for traditional cytogenetic chemical staining. Also, it is difficult for large enough restriction fragments to be extracted from such material for other conventional research tools, such as Southern analysis. However, the nucleic acid from such specimens can be extracted by known techniques such as those described in Greer et al., Anatomic Pathology, 95(2): 117-124 (1991) and Dubeau et al., Cancer Res., 46: 2964-2969 (1986), and if necessary, amplified for testing by various CGH methods. Such nucleic acid can be amplified by using a polymerase chain reaction (PCR) procedure (described above), for example, by the method described in Greer et al., supra wherein DNA from paraffin-embedded tissues is amplified by PCR.

A particular value of testing such archived nucleic acid is that such specimens are usually keyed to the medical records of the patients from whom the specimens were taken. Therefore, valuable diagnostic/prognostic associations can be made between the revealed cytogenetic state of patients' nucleic acid material and the medical histories of treatment and outcome for those patients. For example, information gathered by CGH can be used to predict the invasiveness of a tumor based upon its amplification and/or deletion pattern or sequence characteristics matched to associations made with similar patterns of patients whose outcomes are known.

Analogously, other nucleic acid that is fixed by some method, as, for example, archaeological material preserved through natural fixation processes, can also be studied by CGH procedures. As indicated above, copy number differences between species provide information on the degree of similarity and divergence of the species studied. Evolutionarily important linkages and disjunctions between and among species, extant or extinct, can be made by using the methods of CGH.

Tumor Cytogenetics

CGH provides the means to assess the association between gene amplification and/or deletion and the extent of tumor evolution. Correlation between amplification and/or deletion and stage or grade of a cancer may be prognostically important because such information may contribute to the definition of a genetically based tumor grade that would better predict the future course of disease with more advanced tumors having the worst prognosis. In addition, information about early amplification and/or deletion events may be useful in associating those events as predictors of subsequent disease progression. Gene amplification and deletions as defined by CGH to, for example, normal metaphase spreads (genomic site, intensity of the signal and/or differences in signal ratios, and number of different genomic sites at which the copy number differences occur) can be associated with other known parameters such as tumor grade, histology, Brd/Urd labeling index, hormonal status, nodal involvement, tumor size, survival duration and other tumor properties available from epidemiological and biostatistical studies. For example, tumor DNA to be tested by CGH could include atypical hyperplasia, ductal carcinoma in situ, stage I-III cancer and metastatic lymph nodes in order to permit the identification of associations between amplifications and deletions and stage.

The associations made may make possible effective therapeutic intervention. For example, consistently amplified regions may contain an overexpressed gene, the product of which may be able to be attacked therapeutically (for example, the growth factor receptor tyrosine kinase, p185.sup.HER2) CGH hybridizations of nucleic acids from cells of primary cancers that have metastasized to other sites can be used to identify amplification and/or deletion events that are associated with drug resistance. For example, the subject nucleic acids to be analysed could be selected so that approximately half are from patients whose metastatic disease responded to chemotherapy and half from patients whose tumors did not respond. If gene amplification and/or deletion is a manifestation of karyotypic instability that allows rapid development of drug resistance, more amplification and/or deletion in primary tumors from chemoresistant patients than in tumors in chemosensitive patients would be expected. For example, if amplification of specific genes is responsible for the development of drug resistance, regions surrounding those genes would be expected to be amplified consistently in tumor cells from pleural effusions of chemoresistant patients but not in the primary tumors. Discovery of associations between gene amplification and/or deletion and the development of drug resistance may allow the identification of patients that will or will not benefit from adjuvant therapy.

Once a new region of amplification or deletion has been discovered by CGH, it can be studied in more detail using chromosome-specific painting [Pinkel et al., PNAS (USA), 85: 9138-9142 (1988); EP Publication No. 430,402 (Jun. 5, 1991)] with a collection of probes that span the amplified or deleted region. Probes to amplified regions will show more signals than centromeric signals from the same chromosome, whereas probes to nonamplified regions will show approximately the same number of test and centromeric signals. For example, the amplified regions on 17q22-23 and 20qter show variability in size from tumor to tumor using CGH (the 17q22-23 region more markedly); it can be expected that the region containing the important gene(s) can be narrowed by mapping the regions of amplification in multiple tumors in more detail to find the portion that is amplified in all cases. Probes for those studies can be selected, for example from specific cosmid libraries produced by the National Laboratory Gene Library Project and/or from the National Institute of Health (NIH) genomic research projects.

The c-erbB-2 oncogene, also referred to as HER-2 or neu, encodes for a 185 kilodalton (Kd) protein. Studies have reported c-erbB-2 gene amplification in human mammary tumor cell lines. [Kraus et al., EMBO J. 6: 605-610 (1987); van de Vijver et al., Mol. Cell Biol., 7: 2019-2023 (1987).]

Also, c-erbB-2 gene amplification in human breast cancer has been shown to be associated with disease behavior, and may be a predictor of clinical outcome. [Slamon et al., Science, 235: 177-182 (1987); Berger et al., Cancer Res., 48: 1238-1243 (1988); Zhou et al., Cancer Res., 47:6123-6125 (1987); and Venter et al., Lancet, 11: 69-71 (1987)]. C-erbB-2 has also been shown to be amplified in ovarian cancers. [Alitalo and Schwab, Advances in Cancer Res., 47: 235-281 (1986).]

C-myc is a proto-oncogene which is the cellular homolog of the transforming gene of the chicken retrovirus MC29. In humans, c-myc lies on the long arm of chromosome 8, at band 124, and spans about 5 kilobase pairs. The myc protein is a phosphoprotein present in the nucleus. The normal function of c-myc is unknown; however, it also certainly plays a role in cell division, and is expressed in normally growing cells as well as in tumor cells. It is now widely believed that translocations involving c-myc lead to altered transcription of the gene, contributing to malignant transformation.

Sequences from N-myc member of the myc gene family have been shown to be amplified as much as a thousandfold in some neuroblastomas. N-myc amplifications are usually seen in the later stage III and IV tumors. Some small-cell lung carcinomas also have amplified myc genes in double minute chromosomes (DMs) and homogeneously staining regions (HSRs). Myc has also been shown to be amplified in colon cancer. [Alitalo and Schwab, supra.] Again such amplifications are found in late stages of tumor development, in the so-called variant cells that exhibit a more malignant behavior. Amplifications can involve either c-myc, N-myc or another member of the myc gene family, L-myc. [Watson et al., supra at pp. 1084-1086].

In addition, overexpression has been observed for the p-glycoprotein gene family associated with multi-drug resistance and for drug metabolizing enzymes such as P450 containing enzymes and glutathione S-transferase. [Fairchild and Cowan, J. Radiation Oncol. Biol. Phys., 20: 361-367 (1990).]

Identification of amplified and/or deleted genes is important to the management of cancer, for example, breast cancer, for several reasons:

(1) to improve prognostication;

(2) to detect amplification and/or deletion events that are associated with the development of drug resistance; and (3) to improve therapy. For example, in regard to improving prognostication, in breast cancer the amplification of oncogenes, such as int-2, erbB-2 and myc occur frequently and have been associated with aggressive growth and poor prognosis in some studies. [Schwab and Amier, Genes, Chromosomes & Cancer, 1: 181-193 (1990).] In regard to reason (2), gene amplification has clearly been shown to lead to drug resistance in vitro (for example, amplification of the dihydrofolate reductase gene confers resistance to methotrexate), and is likely to occur in patients undergoing therapy as well (for example, as a result of over expression of glutathione S-transferase and p-glycoprotein). [Fairchild and Cowan, supra]. Thus, the identification of resistance-linked genes would have a major impact on therapy by allowing therapy modification as resistance-related gene amplification occurs. Therapy could be improved by targeting for specific therapy, tumors that overexpress specific amplified genes.

Prenatal Diagnosis

Prenatal screening for disease-linked chromosome aberrations (e.g., trisomy 21) is enhanced by the rapid detection of such abberrations byCGH. CGH analysis is particularly significant for prenatal diagnosis in that it yields more rapid results than are available by cell culture methods.

Removal of Repetitive Sequences and/or Disabling the Hybridization Capacity of Repetitive Sequences The following methods can be used to remove repetitive sequences and/or disable the hybridization capacity of such repetitive sequences. Such methods are representative and are expressed in terms of procedures well known to those of ordinary skill the art, and which can be modified and extended according to parameters and procedures well known to those in the art.

Bulk Procedures. In many genomes, such as the human genome, a major portion of distributed (or shared) repetitive DNA is contained in a few families of highly repeated sequences such as Alu. These methods primarily exploit the fact that the hybridization rate of complementary nucleic acid strands increases as their concentration increases. Thus, if a mixture of nucleic acid fragments is denatured and incubated under conditions that permit hybridization, the sequences present at high concentration will become double-stranded more rapidly than the others. The double-stranded nucleic acid can then be removed and the remainder used in the hybridizations. Alternatively, the partially hybridized mixture can be used as the subject nucleic acid, the double-stranded sequences being unable to bind to the target. The following are methods representative of bulk procedures that are useful for disabling the hybridization capacity of repetitive sequences or removing those sequences from a mixture.

Self-reassociation. Double-stranded nucleic acid in the hybridization mixture is denatured and then incubated under hybridization conditions for a time sufficient for the high-copy sequences in the mixture to become substantially double-stranded. The hybridization mixture is then applied to the reference chromosome spread. The remaining labeled single-stranded copies of the highly repeated sequences may bind throughout the reference chromosome spread producing a weak, widely distributed signal.

Use of blocking nucleic acid. Unlabeled nucleic acid sequences which are complementary to those sequences in the hybridization mixture whose hybridization capacity it is desired to inhibit are added to the hybridization mixture. The subject nucleic acids and blocking nucleic acid are denatured, if necessary, and incubated under appropriate hybridization conditions. The sequences to be blocked become double-stranded more rapidly than the others, and therefore are unable to bind to the reference spread when the hybridization mixture is applied to the spread. In some cases, the blocking reaction occurs so quickly that the incubation period can be very short, and adequate results can be obtained if the hybridization mix is applied to the spread immediately after denaturation. Further, the probe and the target can be simultaneously denatured in some cases. A blocking method is generally described in the context of Southern analysis by Sealy et al., "Removal of Repeat Sequences form Hybridization Probes", Nucleic Acid Research, 13:1905 (1985). Examples of blocking nucleic acids include genomic DNA, a high-copy fraction of genomic DNA and particular sequences as outlined below.

i. Genomic DNA. Genomic DNA contains all of the nucleic acid sequences of the organism in proportion to their copy-number in the genome. Thus, adding genomic DNA to the hybridization mixture increases the concentration of the high-copy repeat sequences more than low-copy sequences, and therefore is more effective at blocking the former.

ii. High-copy fraction of genomic DNA. Fractionating the genomic DNA to obtain only the high-copy sequences and using them for blocking can be done, for example, with hydroxyapatite as described below.

Removal of Sequences

Hydroxyapatite. Single- and double-stranded nucleic acids have different binding characteristics to hydroxyapatite. Such characteristics provide a basis commonly used for fractionating nucleic acids. Hydroxyapatite is commerically available [e.g., Bio-Rad Laboratories, Richmond, Calif. (USA)]. The fraction of genomic DNA containing sequences with a particular degree of repetition, from the highest copy-number to single-copy, can be obtained by denaturing genomic DNA, allowing it to reassociate under appropriate conditions to a particular value of $C_{o\ t}$, followed by separation using hydroxyapatite. The single- and double-stranded nucleic acid can also be discriminated by use of S1 nuclease. Such techniques and the concept of $C_{o\ t}$ are explained in Britten et al., "Analysis of Repeating DNA Sequences by Reassociation", in Methods in Enzymology, 29: 363-418 (1974).

Reaction with immobilized nucleic acid. Removal of particular sequences can also be accomplished by attaching single-stranded "absorbing" nucleic acid sequences to a solid support. Single-stranded source nucleic acid is hybridized to the immobilized nucleic acid. After the hybridization, the unbound sequences are collected and used in CGH. For example, human genomic DNA can be used to absorb repetitive sequences from the subject nucleic acids. One such method is described by Brison et al., "General Method for Cloning Amplified DNA by Differential Screening with Genomic Probes," Molecular and Cellular Biology, 2: 578-587 (1982). Briefly, minimally sheared human genomic DNA is bound to diazonium cellulose or a like support. The source DNA, appropriately cut into fragments, is hybridized against the immobilized DNA to $C_{o\ t}$ values in the range of about 1 to 100. The preferred stringency of the hybridization conditions may vary depending on the base composition of the DNA.

Prehybridization. Blocking of repeat sequence binding sites in the reference genome by hybridization with unlabeled complementary sequences will prevent binding of labeled sequences in the subject nucleic acids that have the potential to bind to those sites. For example, hybridization with unlabeled genomic DNA will render the high-copy repetitive sequences in the reference genome double-stranded. Labeled copies of such sequences in the subject nucleic acids will not be able to bind when they are subsequently applied.

In practice, several mechanisms can be combined to produce the desired contrast and sensitivity.

Labeling the Nucleic Acid Fragments of the Subject Nucleic Acids

There are many techniques available for labeling single- and double-stranded nucleic acid fragments of the subject nucleic acids. They include incorporation of radioactive labels, e.g. Harper et al. Chromosoma, 83: 431-439 (1984); direct attachment of fluorochromes or enzymes, e.g. Smith et al., Nuc. Acids Res., 13: 2399-2412 (1985), and Connolly et al., Nuc. Acids Res., 13: 4485-4502 (1985); and various chemical modifications of the nucleic acid fragments that render them detectable immunochemically or by other affinity reactions, e.g. Tchen et al., "Chemically Modified Nucleic Acids as Immunodetectable Probes in Hybridization Experiments," PNAS, 81: 3466-3470 (1984); Richardson et al., "Biotin and Fluorescent Labeling of RNA Using T4 RNA Ligase," Nuc. Acids Res., 11: 6167-6184 (1983); Langer et al., "Enzymatic Synthesis of Biotin-Labeled Nucleic acids: Novel Nucleic Acid Affinity Probes," PNAS, 78: 6633-6637 (1981); Brigati et al., "Detection of Viral Genomes in Cultured Cells and Paraffin-Embedded Tissue Sections Using Biotin-Labeled Hybridization Probes," Virol., 126: 32-50 (1983); Broker et al., "Electron Microscopic Visualization of tRNA Genes with Ferritin-Avidin: Biotin Labels," Nuc. Acids Res., 5: 363-384 (1978); Bayer et al., "The Use of the Avidin Biotin Complex as a Tool in Molecular Biology," Methods of Biochem. Analysis, 26: 1-45 (1980); Kuhlmann, Immunoenzyme Techniques in Cytochemistry (Weinheim, Basel, 1984). Langer-Safer et al., PNAS (USA), 79: 4381 (1982): Landegent et al., Exp. Cell Res., 153: 61 (1984); and Hopman et al., Exp. Cell Res., 169: 357 (1987). Thus, as indicated, a wide variety of direct and/or indirect means are available to enable visualization of the subject nucleic sequences that have hybridized to the reference genome. Suitable visualizing means include various ligands, radionuclides, fluorochromes and other fluorescers, chemiluminescers, enzyme substates or co-factors, particles, dyes and the like. Some preferred exemplary labeling means include those wherein the probe fragments are biotinylated, modified with N-acetoxy-N-2-acetylaminofluorene, modified with fluorescein isothiocyanate or other fluorochromes, modified with mercury/TNP ligand, sulfonated, digoxigeninated or contain T-T dimers.

A preferred method of labeling is tailing by terminal transferase labeling. Another preferred method is random priming with mixed sequence primers followed by polymerase extension. This has the additional feature of amplifying the amount of subject DNA.

The key feature of labeling is that the subject nucleic acid fragments bound to the reference spread be detectable. In some cases, an intrinsic feature of the subject nucleic acid, rather than an added feature, can be exploited for this purpose. For example, antibodies that specifically recognize RNA/DNA duplexes have been demonstrated to have the ability to recognize probes made from RNA that are bound to DNA targets [Rudkin and Stollar, Nature, 265:472-473 (1977)]. The RNA used is unmodified. Nucleic acid fragments can be extended by adding "tails" of modified nucleotides or particular normal nucleotides. When a normal nucleotide tail is used, a second hybridization with nucleic acid complementary to the tail and containing fluorochromes, enzymes, radioactivity, modified bases, among other labeling means, allows detection of the bound nucleic acid fragments. Such a system is commercially available from Enzo Biochem [Biobridge Labeling System; Enzo Biochem Inc., New York, N.Y. (USA)].

Another example of a means to visualize the bound nucleic acid fragments wherein the nucleic acid sequences do not directly carry some modified constituent is the use of antibodies to thymidine dimers. Nakane et al., ACTA Histochem. Cytochem., 20 (2):229 (1987), illustrate such a method wherein thymine-thymine dimerized DNA (T-T DNA) was used as a marker for in situ hybridization. The hybridized T-T DNA was detected immunohistochemically using rabbit anti-T-T DNA antibody.

All of the labeling techniques disclosed in the above references may be preferred under particular circumstances. Further, any labeling techniques known to those in the art would be useful to label the subject nucleic acids. Several factors govern the choice of labeling means, including the effect of the label on the rate of hybridization and binding of the nucleic acid fragments to the chromosomal DNA, the accessibility of the bound nucleic acid fragments to labeling moieties applied after initial hybridization, the mutual compatibility of the labeling moieties, the nature and intensity of the signal generated by the label, the expense and ease in which the label is applied, and the like.

Several different subject nucleic acids, each labeled by a different method, can be used simultaneously. The binding of different nucleic acids can thereby be distinguished, for example, by different colors.

In Situ Hybridization

Application of the subject nucleic acids to the reference chromosome spreads is accomplished by standard in situ hybridization techniques. Several excellent guides to the technique are available, e.g., Gall and Pardue, "Nucleic Acid Hybridization in Cytological Preparations," Methods in Enzymology, 21: 470-480 (1981); Henderson, "Cytological Hybridization to Mammalian Chromosomes," International Review of Cytology, 76: 1-46 (1982); and Angerer et al., "in situ Hybridization to Cellular RNAs," in Genetic Engineering: Principles and Methods, Setlow and Hollaender, Eds., Vol. 7, pgs. 43-65 (Plenum Press, New York, 1985).

Generally in situ hybridization comprises the following major steps: (1) fixation of tissue or biological structure to be examined, (2) prehybridization treatment of the biological structure to increase accessibility of target DNA, and to reduce nonspecific binding, (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments. The reagents used in each of these steps and their conditions of use vary depending on the particular situation.

Under the conditions of hybridization wherein human genomic DNA is used as an agent to block the hybridization capacity of the repetitive sequences, the preferred size range of the nucleic acid fragments is from about 200 bases to about 1000 bases, more preferably about 400 to 800 bases for double-stranded, nick-translated nucleic acids and about 200 to 600 bases for single-stranded or PCR adapter-linker amplified nucleic acids.

Basically the same hybridization protocols as used for chromosome-specific painting as described in Pinkel et al., PNAS (USA), 85: 9138-9142 (1988) and in EP Pub. No. 430,402 (published Jun. 5, 1991) can be adapted for use in CGH.

Array CGH

In a preferred embodiment, nucleotide sequence differences are detected, according to the invention, using array CGH. To carry out array CGH, target solutions are prepared from starting nucleic acids and applied to a substrate to form a nucleic acid array. Sample nucleic acids are prepared, labeled, and hybridized to the array. The signal produced by the hybridized nucleic acids is then detected an analyzed.

Preparation of Target Solutions

Any type of nucleic acid can be employed as the starting nucleic acid in the methods of the invention. Typically, the starting nucleic acid is a DNA molecule, which can be obtained by any available means. The nucleic acid can a have sequence corresponding to a natural nucleic acid sequence found in any organism, typically vertebrates, preferably birds or mammals, more preferably animals having research or commercial value, such as mice, rats, guinea pigs, rabbits, cats, dogs, chickens, pigs, sheep, goats, cows, horses, as well as monkeys and other primates, including humans. Organisms for which there are established inbred strains, such as rats or mice, are preferred for use in some embodiments, such as that illustrated in Example 3. Lists of such hundreds of strains are publicly available, see, for example, http://www.informatics.jax.org/external/festing/mouse/STRAINS.shtml. A list of exemplary mouse strains useful in the invention is also given below in Table 1. In preferred embodiments, the starting nucleic acid is a genomic DNA molecule.

In preferred embodiments, each of the starting nucleic acids is derived from a defined region of the genome (for example, a clone or several contiguous clones from a genomic library) or corresponds to an expressed sequence (for example, a full-length or partial cDNA). The nucleic acids can also comprise amplification products, such as inter-Alu or degenerate oligonucleotide primer PCR products.

Nucleic acids of unknown significance can also be employed in the methods of the invention. An array of such nucleic acids could represent locations that sample, either continuously or at discrete points, any desired portion of a genome, including, but not limited to, an entire genome, a single chromosome, or a portion of a chromosome. The number of nucleic acid elements in the array and the complexity of the nucleic acids would determine the density of sampling. For example, an array of 300 elements, each element containing DNA from a different genomic clone, could sample the entire human genome at 10 megabase (Mb) intervals. An array of 30,000 elements, each containing 100 kb of genomic DNA could give complete coverage of the human genome. In specific embodiments, the method of the invention employ genomic DNA arrays of at least about 1000, at least about 5000, or at least about 10,000 different element corresponding to different loci in a genome of interest.

In preferred embodiments, the starting nucleic acids are derived from a nucleic acid library. The nucleic acid library can be a genomic DNA library, a cDNA library, or simply a collection of genomic or cDNA molecules or nucleic acids amplified from a sample. Although libraries using any type of cloning vector, such as eukaryotic (e.g., yeast), procaryotic, or viral vectors, can be employed in the methods of the invention, the methods are particularly useful for producing target solutions from YAC, BAC, P1, PAC, cosmid, or cDNA libraries. YAC, BAC, P1, and PAC vectors are designed to accommodate very large (i.e., up to several hundred kb) inserts.

For most applications, the starting nucleic acids each have a complexity of greater than 20 bases. In specific embodiments, the starting nucleic acids each have a complexity of at least about 1, 5, 10, 20, 30, 40, and 50 kb, and more preferably at least about 100, 200, 300, 400, and 500 kb. For most applications, the complexity is less than about 1.1 Mb but the methods of the invention can be applied to higher complexity nucleic acids, if desired. In preferred embodiments, the target solutions produced from the starting nucleic acids retain essentially the same complexity and are used to fabricate arrays in which the sequence complexity of each target element typically greater than 20 bases and, in specific embodiments, about 1, 5, 10, 20, 30, 40, 50, and 75 kb, or more preferably at least about 100, 200, 300, 400, and 500 kb. Generally, the complexity of each target element need not exceed 1.1 Mb.

Ligation-Mediated Amplification of Nucleic acids for Target Solutions

Nucleic acids can be prepared for target solutions, using any of a number of standard techniques (see U.S. Pat. No. 5,830,645, issued to Pinkel et al. on Nov. 3, 1998). In one embodiment, the target solutions are prepared using a ligation-mediated amplification procedure described by Klein, C. A., et al. (1999) Proc. Natl. Acad. Sci. USA 96:4494-4499 for global amplification of DNA from single eukaryotic cells. Ligation-mediated PCR requires double-stranded nucleic acid fragments, preferably having 5' or 3' extensions. Adapters are ligated to each end of the nucleic acid fragments, which provides the fragments with common priming sites for amplification. Adapters are typically designed to serve as efficient amplification primers so that unligated strands of the adapters can be employed to amplify the sequences between the priming sites. This approach allows amplification of any nucleic acid without prior knowledge of the nucleotide sequence and allows the production of amplification products that are representative of the starting nucleic acid used as the amplification template.

The starting material for amplifying nucleic acids for target solutions of the invention is a plurality of samples of double-stranded nucleic acid fragments. Each sample of nucleic acid fragments is derived from a starting nucleic acid, i.e., one whose sequences are to be included at a distinct location in the array. The starting nucleic acids are obtained by any standard procedure that produces nucleic acids sufficiently free of contaminants to allow the generation of nucleic acid fragments that can be amplified. Where the starting nucleic acid is a recombinant clone, for example, the nucleic acid is preferably substantially free of host cell DNA and non-nucleic acid contaminants. Example 1 describes the isolation of BAC clones by standard alkaline lysis.

Blunt-ended fragments can be employed in ligation-mediated amplification, but fragments having common 5' or 3' extensions are preferred. Double-stranded nucleic acid fragments with 5' or 3' extensions are most conveniently obtained by digesting each starting nucleic acid with a restriction endonuclease that produces such fragments. A large number of restriction enzymes are available, and many suitable for use in the claimed method are described in Sambrook et al. (1989) Molecular Cloning: A Laboratory Manual, 2nd Edition (Cold Spring Harbor Laboratory Press).

The restriction enzyme employed preferably has a cutting frequency such that it is expected to produce nucleic acid fragments that are small enough to allow amplification using standard techniques. Preferably, nucleic acid fragments having an average length of less than about 5 kilobases (kb), more preferably less than about 2 kb, are generated for use in the method of the invention. Typically, the average length of such nucleic acid fragments is greater than about 50 basepairs (bp). The cutting frequencies of the available restriction enzymes can be determined statistically to identify restriction enzymes that produce fragments in this range of sizes. If a given restriction enzyme has too few or too many cutting sites in a nucleic acid, the selection of an alternate enzyme (or an additional enzyme, in the case of too few cutting sites) is within the level of skill in the art. Restriction enzymes used for ligation mediated PCR typically have at least 4-base cleavage sites, and preferably 4-, 5-, or 6-base cleavage sites. Examples of suitable restriction enzymes include the following 4-base cutters: CviII, MnII, AluI, BsuFI, HapII, HpaII, MseI, MspI, AccII, BstUI, BsuEI, FnuDII, ThaI, Bce243I, BsaPI, Bsp67I, BspAI, BspPII, BsrPII, BssGII, BstEIII, BstXII, CpaI, CviAI, DpnII, FnuAII, FnuCI, FnuEI, MboI, MmeII, MnoIII, MosI, MthI, NdeII, NflI, NlaII, NsiAI, NsuI, PfaI, Sau3AI, SinMI, HhaI, HinPI, BsuRI, HaeIII, NgoII, CviQI, RsaI, TaqI, and TthHBI.

More than one restriction endonuclease can be employed, if desired. Depending on the combination of restriction enzymes, an additional primer(s) may be required to ensure that all fragments are amplified to produce an amplification product that is representative of the starting nucleic acid.

Restriction digests are carried out under standard conditions, usually those recommended by the manufacturer.

After obtaining samples of double-stranded nucleic acid fragments corresponding to each starting nucleic acid, adapters are added to each end of the nucleic acid fragments to produce modified nucleic acid fragments. The considerations for designing adapters suitable for use in the present invention do not differ from those in standard ligation-mediated amplification procedures. See, e.g., Klein, C. A., et al. (1999) Proc. Natl. Acad. Sci. USA 96:4494-4499; Smith, D. R. (1992) PCR Methods and Applications 2:21-27.

In particular, adapters contain two nucleic acid strands, one or both of which is/are capable of serving as amplification primers. The second strand has a first region of substantial complementarity to a first region of the first strand. This region serves as the priming site for amplification. For blunt-ended nucleic acid fragments, the adapters are simply ligated to the blunt ends. For nucleic acid fragments with cohesive ends, the adapters are annealed to the 5' or 3' extensions of each nucleic acid fragment. Thus, one strand of each adapter also contains a second region that is substantially complementary to a region in the extensions of the nucleic acid fragments. Adapters useful in ligation-mediated amplification are typically designed so that contact with a ligase results in ligation of only one strand to each end of the nucleic acid fragments.

Conditions for annealing the adapter to the nucleic acid fragments, such as temperature, ionic strength, and oligonucleotide concentrations are generally selected to provide appropriate specificity of hybridization. Conditions suitable for annealing a given adapter to a particular 5' or 3' extension sequence are either known or can readily be determined by those skilled in the art.

The annealed adapters are contacted with a nucleic acid ligase, such as T4 nucleic acid ligase under suitable conditions, and for a sufficient time, to ligate an end of one strand of the adapters to an adjacent end of the nucleic acid fragment. This ligation is generally carried out according to standard techniques, i.e., in an appropriate ligation buffer including ATP. In ligation-mediated amplification, annealing of the adapters is performed by raising and then lowering the temperature of the mixture, followed by addition of ligase.

After ligation, the reaction mixture is generally denatured to remove the unligated adapter strand and the gap left is filled in by adding a suitable polymerase, such as Taq and/or Pwo, and dNTPs. The unligated adapter strand is then available for use as an amplification primer. As discussed in greater detail below, this primer can contain a functional group (such as an amino group) that facilitates immobilization of nucleic acids to a substrate. The sequences between the priming sites are amplified in a conventional amplification reaction. The selection of amplification protocols for various applications are well known to those of skill in the art. Guidance regarding various in vitro amplification methods can be found, for example, in Sambrook (1989) Molecular Cloning: A Laboratory Manual, 2nd Edition (Cold Spring Harbor Laboratory Press); U.S. Pat. No. 4,683,202 (issued in 1987 to Mullis et al.) ; PCR Protocols A Guide to Methods and Applications (Innis et al. eds) Academic Press Inc. San Diego, Calif. (1990); Armheim & Levinson (Oct. 1, 1990) C&EN 36-47; The Journal Of NIH Research (1991) 3: 81-94; (Kwoh et al. (1989) Proc. Natl. Acad. Sci. USA 86: 1173; Guatelli et al. (1990) Proc. Natl. Acad. Sci. USA 87, 1874; Lomell et al. (1989) J. Clin. Chem., 35: 1826; Landegren et al., (1988) Science, 241: 1077-1080; Van Brunt (1990) Biotechnology, 8: 291-294; Wu and Wallace, (1989) Gene, 4: 560; and Barringer et al. (1990) Gene, 89: 117; as well as Smith, D. R. (1992) PCR Methods and Applications 2:21-27.

Preferably, the polymerase chain reaction (PCR) is used to amplify the nucleic acid fragments. For PCR, dNTPs, and one or more polymerases, such as Taq and/or Pwo polymerases, are added to the reaction mixture, which is then subjected to temperature cycling to allow repeated sequences of denaturation, primer annealing, and nucleic acid synthesis. An exemplary, preferred PCR amplification protocol is described in Example 1. This step produces an amplification product for each sample of nucleic acid fragments that is derived from a starting nucleic acid, such as a BAC clone. To fabricate an array containing 30,000 BAC clones, for example, each clone could be digested with a restriction enzyme and each of the resulting samples of nucleic acid fragments would be amplified to produce 30,000 amplification products.

If larger amounts of amplification products are desired, one or more additional rounds of amplification can be performed using the amplification products from the prior round of amplification as a template. An exemplary protocol including two rounds of amplification is described in Example 1. This feature of the method is particularly advantageous when preparing target solutions of nucleic acids from single-copy vectors, such as BACs, for which it is otherwise necessary to grow large cultures to obtain sufficient DNA for arraying.

Target Solutions

To form target solutions, the nucleic acid products of ligation-mediated amplification are isolated by any convenient method, such as, for example, precipitation by ethanol. Each nucleic acid product is resuspended to form a target solution suitable for application to a substrate. Suitable solutions should not significantly diminish the hybridization capacity of the nucleic acid products and should enable the nucleic acid products to adhere to the substrate.

Suitable solutions are well known to those of skill in the art and include, for example, 3×SSC and solutions containing one or more denaturants, such as formamide or dimethyl sulfoxide (e.g., 50% vol/vol DMSO in water). A 20% vol/vol DMSO solution is better at solubilizing DNA than solutions containing more DMSO and is preferred. Target solutions intended for robotic spotting of microarrays preferably have a sufficiently low viscosity to allow spotting using conventional robotic techniques. In some embodiments, reproducible spotting of a precise amount of a target solution containing a predetermined amount of nucleic acids is desirable; however, differences in the amount of target solutions spotted can be normalized by including a control in the hybridization study, as is done, for example, in CGH.

The concentration of the nucleic acid in the target solution should be high enough to allow detection of a hybridization signal from the corresponding target element of the array. Generally, good results are obtained using target solutions that have nucleic acid concentrations of about 0.2 µg/µl to about 2 µg/µl. Higher nucleic acid concentrations can be employed; however, improvements in signal level off at a nucleic acid concentration of about 1 µg/µl.

In one embodiment, the invention provides a collection of target solutions that is representative of a collection of YAC, BAC, P1, PAC, or cosmid clones.

Preparation of Nucleic Acid Arrays

Application of Target Solutions to a Substrate

The target solutions of the invention can each be applied to a distinct location on a substrate to produce an array of nucleic acid-containing target elements. Substrates suitable for arraying nucleic acids are well-known and include, for example, a membrane, glass, quartz, or plastic. Exemplary membranes include nitrocellulose, nylon, diazotized membranes (paper or nylon), silicones, polyformaldehyde, cellulose, cellulose acetate, and the like. The use of membrane substrates (e.g., nitrocellulose, nylon, polypropylene) is advantageous because of well-developed technology employing manual and robotic methods of arraying targets at relatively high element densities. In addition, such membranes are generally available, and protocols and equipment for hybridization to membranes are well-known. Plastics suitable for use as array substrates include polyethylene, polypropylene, polystyrene, and the like. Other materials, such as ceramics, metals, metalloids, and semiconductive materials, can also be employed. In addition substances that form gels can be used. Such materials include proteins (e.g., gelatins), lipopolysaccharides, silicates, agarose and polyacrylamides. Where the substrate is porous, various pore sizes can be employed depending upon the nature of the system. Exemplary, preferred substrates include aminosilane, poly-lysine, and chromium substrates.

Substrates useful in the invention can have any convenient shape. Although the substrate typically has at least one flat, planar surface, substrates with non-planar surfaces are also within the scope of the invention. For example, the substrate can be made from beads, pins, or optical fibers.

Many methods for immobilizing nucleic acids on a variety of substrates are known in the art. The nucleic acid products described herein can be covalently or noncovalently bound to the substrate. The substrate surface can be prepared for immobilization using any of a variety of different materials, for example as laminates, depending on the desired properties of the array. Proteins (e.g., bovine serum albumin) or mixtures of macromolecules (e.g., Denhardt's solution) can be employed to avoid non-specific binding, simplify covalent conjugation, enhance signal detection or the like. If covalent bonding between a nucleic acid and the substrate surface is desired, the surface can be polyfunctional or capable of being polyfunctionalized. Functional groups useful for covalently bonding nucleic acids to substrate surfaces include carboxylic acids, aldehydes, amino groups, cyano groups, ethylenic groups, hydroxyl groups, mercapto groups, and the like. Alternatively, such functional groups can be introduced into the nucleic acid products of the invention. Methods for introducing various functional groups into nucleic acids are well-known and described, for example, in Bischoff et al., Anal. Biochem. (1987) 164:336-344; Kremsky et al., Nuc. Acids Res. (1987) 15:2891-2910. Nucleotides bearing functional groups can also added to the products of the ligation-mediated amplification method described above using PCR primers containing a modified nucleotide, or by enzymatic end-labeling with modified nucleotides. In a preferred embodiment, nucleic acid products according to the invention bear a functional group, such as, for example, an amino group.

The target solutions are applied to the substrate surface using any method that substantially maintains the hybridization capacity of the target nucleic acids. For fabrication of microarrays, the target solutions are applied by robotic spotting using a device such as that described in U.S. Pat. No. 5,807,522 (issued Sep. 15, 1998 to Brown and Shalon). The target solutions can be applied, for example, by tapping a capillary dispenser containing target solution against the substrate surface. To form a microarray, the average volume of each target solution applied to the substrate is less than about 2 nanoliters. Generally, at least about 0.002 nanoliters of each target solution is applied to the substrate. Preferably, between about 0.02 nanoliters and about 0.2 nanoliters of each target solution is applied.

A "print head" containing multiple, closely spaced dispensers or "printing tips" can be employed to facilitate array manufacture and to minimize the physical size of arrays, thereby reducing the amounts of nucleic acids required for each hybridization analysis. An exemplary system for fabricating a microarray by robotic spotting is described in Example 2.

Arrays

Arrays prepared as described above have target elements containing nucleic acids that are each representative of the nucleic acid from which the corresponding target element nucleic acids are derived (i.e, by amplification). In one embodiment, the invention provides an array in which each target element is representative of a YAC, BAC, P1 and/or PAC clone.

An array useful in the invention can include target elements of any dimensions suitable for the intended application. Small target elements containing small amounts of concentrated target nucleic acids are conveniently used when the labeled nucleic acids that are hybridized to them contain high complexity nucleic acids, since the total amount of labeled nucleic acid available for binding to each target element during hybridization to the array will be limited. Such target elements also provide a hybridization signal that is highly localized and bright. Thus, target elements of less than about 1 cm in diameter are generally preferred. Exemplary target element sizes range from 1 µm to about 3 mm, and are preferably between about 5 µm and about 1 mm.

Target element density depends upon a number of factors, such as the substrate, the technique for applying target solutions to the substrate, the nature of the label to be hybridized to the array, and the like. Microarrays have target element densities of at least 100 target elements per $cm^2$ of substrate. Preferred microarrays have target element densities of at least $10^3$, $10^4$, $10^5$, and $10^6$ target elements per $cm^2$ of substrate.

Preparation of Sample Nucleic Acids

As with target nucleic acids, a wide variety of nucleic acids can be used as sample nucleic acids in the methods of the present invention. The sample nucleic acids can include non-natural sequences or natural nucleic acid sequences derived from any organism, typically vertebrates, preferably birds or mammals, more preferably animals having research or commercial value, such as mice, rats, guinea pigs, rabbits, cats, dogs, chickens, pigs, sheep, goats, cows, horses, as well as monkeys and other primates, including humans. In specific embodiments, one or both samples can be samples of DNA molecules.

The sample nucleic acids may include, for example, genomic DNA representing the entire genome from a particular organism, tissue, or cell type or may include a portion of the genome, such as a single chromosome. For some applications, it may be desirable to use RNA samples, to take advantage of differences in the hybridization characteristics of DNA:DNA hybrids versus DNA:RNA hybrids. In this case, DNA samples could still analyzed by synthesizing RNA from a DNA template. This could be accomplished using known techniques, such as the use of an RNA polymerase to synthesize RNA from vectors that include an RNA promoter oriented to transcribe a DNA sequence cloned into the vector.

The methods of the invention are suitable for detecting sequence differences in any combination of two or more samples of nucleic acids. The method is particularly well-suited to identifying small sequence differences in relatively complex samples that have a low sequence divergence. Thus, sample complexities can be at least about: 1, 5, 10, 50, 100, 500, 1000, 5000, $10^4$, $5\times10^4$, $10^5$, $5\times10^5$, or $10^6$ kilobases or any range having any of these listed values as endpoints. In preferred embodiments, one or both samples can include entire genomes (e.g., approximately $3\times10^6$ kilobases). In particular embodiments, the sequence divergence between two nucleic acid samples being compared is less than about 10%, typically less than about 5%, preferably less than about 2%, and more preferably less than about 1%, 0.9%, 0.8%, 0.7%, 0.6%, 0.5%, 0.4%, 0.3%, 0.2%, or 0.1%.

In specific embodiments, sample nucleic acids from two different species or from the same species can be compared. Preferred intra-species comparisons include comparisons between sample nucleic acids from two different strains. In preferred embodiments, the sample nucleic acids are derived from related individuals. An exemplary, preferred variation of this embodiment is described in Example 3, in which one sample is from a parental strain or species that is crossed with another strain or species to produce an F1 individual, and the other sample is from an individual resulting from the backcross of the F1 individual with one of the parental strains or species. As illustrated in Example 3, the hybridization of two such differently labeled samples to a genomic DNA array allows a determination as to whether the backcross individual is homozygous or heterozygous for each genomic locus represented in the array. This embodiment can be employed using samples from parental, F1 and backcross individuals that differ with respect to a particular characteristic such as disease susceptibility. This embodiment is particularly useful for mapping the locations of putative disease genes. Current mapping procedures are much more labor intensive than this approach, requiring individual analysis of each locus or development of specific arrays based on known sequence differences. This embodiment can be practiced using different strains or related species. Organisms for which there are established inbred strains, such as rats or mice, are preferred. Lists of such hundreds of strains are publicly available, see, for example, http://www.informatics.jax.org/external/festing/mouse/STRAINS.shtml. A list of exemplary mouse strains useful in the invention is also given below in Table 1.

TABLE 1

Exemplary Inbred Mouse Strains

| | | | | | | | |
|---|---|---|---|---|---|---|---|
| 101 | 102 | 129 | 201 | 615 | A | A2G | AA |
| AB | ABH | ABJ | ABL | ABP | ACR | AE | AEJ |
| AG | AKR | AKXL | AL | AM | AMMS | APN | APS |
| AS | AT | ATEB | AU | AX | AXB | AY | B6NXC3N |
| BA | BAB | BALB | BBT | BDP | BFM | BIMA | BIR |
| BL | BLN | BLRB | BN | BNT | BOB | BOMG | BPH |
| BPL | BPN | BRSUNT | BRVR | BRX58N | BSC | BSVR | BSVS |
| BT | BTBRTF | BUA | BUB | BXD | BXH | BXSB | BXVII |
| C | C1 | C17 | C2 | C3H | C3HA | C57BL | C57BLKS |
| C57BR | C57L | C57P | C58 | CASA | CAST | CAT | CBA |
| CBRB | CBXC | CBXNO | CC57BR | CC57W | CE | CF1 | CFCW |
| CFO | CFW | CHI | CHMU | CKB | CL | CLA | CN |
| CPB | CRM | CS | CT | CTA | CWD | CXB | CXS |
| D103 | DA | DBA | DC | DD | DDD | DDI | DDK |
| DDN | DDP | DDY | DE | DF | DH | DHS | DK |
| DKI | DL | DLS | DM | DMC | DOPG | DRC | DSD |
| DTB | DW | EBT | EL | F | FL | FM | FRG |
| FS | FSB | FTC | FVB | G | GL | GLF | GRS |
| GT | H1 | H2 | HC | HDA32 | HLC | HLG | HLS |
| HPG | HPT | HR | HRA | HRS | HSFR | HSFS | HTG |
| HTH | HTI | HYIII | I | IAH | IC | ICFW | ICGN |
| ICR | ICRC | ICW | IDH2 | IF | IITES | ILS | IM |
| IOR | IQI | IS | ISS | ITES | IVCE | IVCS | IXBL |
| J | JBT | JE | JGBF | JIGR | JU | K | KC |
| KE | KF | KI | KK | KP | KR | KSB | KSN |
| KYF | L1 | L2 | LCS | LDJ | LG | LIBP | LIS |
| LLC | LM | LMM | LP | LPT | LS | LST | LSXSS |
| LT | LTS | MA | MAS | MB | MH | MIG | MIW |
| MK | MM | MO | MOA | MOC | MOLC | MOLD | MOLG |
| MOM | MOR2 | MRL | MS | MSM | MT | MTH | MWT |
| MY | MYD | N | NAKED | NBL | NBR | NC | NCU |
| ND2 | NFR | NFS | NGP | NH | NIH | NJS | NLC |
| NMRI | NOD | NON | NOR1 | NOR2 | NOXCB | NRH | NSY |
| NX129 | NXSM | NYLR | NZB | NZBR | NZC | NZM | NZO |
| NZW | NZX | NZY | O20 | OIR | OUBCr | OUBW | OUCW |
| OUF | OUGW | OUYW | P | PAA | PAB | PAC | PAD |
| PBA | PBB | PE | PERA | PERU | PET | PF | PH |
| PHH | PHL | PIC | PL | PM | PN | PRO | PT |
| PUC | PUH | PWD | PWK | QC | QF | RAP | RB |
| RBA | RBB | RBC | RBD | RBE | RBF | RBG | RBJ |
| RC | RF | RFM | RHJ | RIII | RIIIS | RLC | RNC |
| ROP | RR | RSV | RW | S | SAMP1 | SAMP10 | SAMP2 |
| SAMP3 | SAMP6 | SAMP7 | SAMP8 | SAMR1 | SB | SC | SD |
| SEA | SEC | SELH | SEN | SF | SHI | SHM | SHN |
| SHR | SIIT | SIM | SJL | SK | SL | SLN | SM |
| SMXA | SPE | SRH | SRL | SS | SSIN | SSL | ST |
| STAR | STR | STS | STU | STX | SUMS | SWJ | SWM |
| SWR | SWV | SWXJ | SWXL | SXC | SZA | SZB | SZC |
| Swiss | T739 | TA1 | TA2 | TB | TF | TFH | TFM |
| TH | TKDU | TL | TM | TP | TPS | TR | TRE |
| TS | TSI | TSJ | TT6 | UMB | UMC | UMCBE | UMDH |
| UMG | UMS | UMZ | UW | V | VC | VL | VM |
| VP | VY | WB | WC | WH | WHT | WK | WLA |
| WLHR | WLL | WN | WR | X | XLII | XVII | YBR |
| YPC | YS | YT | YX | | | | |

The method of the invention is also useful for detecting loss of heterozygosity at one or more loci of interest. If, for example, one of two different alleles at a particular locus is associated with resistance to disease, the loss of that allele and its replacement with an additional copy of the second allele will be correlated with the development of the disease. Conversely, if the second allele is permissive or stimulatory with respect to the disease, the conversion of the formerly heterozygous locus to one that is homozygous for the second allele will also be correlated with the development of the disease. Thus, loss of heterozygosity can be used to identify loci that may influence the risk of developing a disease that may be linked to such a locus.

In specific embodiments, loss of heterozygosity can be detected by performing a CGH comparison of sample nucleic acids from the same species. In preferred embodiments, the sample nucleic acids are derived from related individuals. Thus, for example, a first sample can include nucleic acids from a first F1 individual produced by crossing a first parental strain with a second (different) parental strain. In theory, this individual should have one allele derived from the first parental strain and one allele derived from the second parental strain and therefore is heterozygous at loci where the strains differ. In actuality, recombination can occur, in which a region of a chromosome is lost and the corresponding region of the other chromosome is duplicated, thus converting a previously heterozygous locus or loci to a homozygous one(s). Such recombination events are often associated with disease, such as cancers in which tumors contain homozygous loci corresponding to genes that influence the development of the cancer, and the normal tissue is heterozygous at these loci.

Sample nucleic acids from the first F1 individual can be analyzed by CGH to determine whether one or more loci, which theoretically should be heterozygous, are in fact homozygous. If that F1 individual differs with respect to some characteristic, such as e.g., disease susceptibility, any locus where loss of heterozygosity occurs is a candidate for containing one or more disease gene. Sample nucleic acids from the first F1 individual can be compared with nucleic acids from any other source that allows detection of loss of heterozygosity in the first F1 individual. Thus, for example, the second (comparison) sample can include nucleic acids from either parental strain or from a second F1 individual. If two different F1 individuals are compared, loss of heterozygosity at loci in each individual can be identified.

In another embodiment, loss of heterozygosity can be detected by comparing sample nucleic acids from normal tissue from an F1 individual with sample nucleic acids from a tumor from that individual.

Standard procedures can be used to isolate nucleic acids from appropriate tissues (see, e.g., Sambrook, et al., Molecular Cloning—A. Laboratory Manual, Cold Spring Harbor Laboratory, Cold Spring Harbor, N.Y. (1985)). The particular cells or tissue from which the nucleic acids are isolated will depend upon the particular application.

If the tissue sample is small, so that a small amount of nucleic acids is available, amplification techniques such as the polymerase chain reaction (PCR) using degenerate primers can be used. For a general description of PCR, see, PCR Protocols, Innis et al. eds. Academic Press, 1990. In addition, PCR can be used to selectively amplify sequences between high-copy repetitive sequences. These methods use primers complementary to highly repetitive interspersed sequences (e.g., Alu) to selectively amplify sequences that are between two members of the Alu family (see, Nelson et al., Proc. Natl. Acad. Sci. USA 86:6686 (1989)).

In preferred embodiments, the sample nucleic acids are derived from a nucleic acid library. The nucleic acid library can, for example, be a collection of cloned genomic DNA molecules, or simply a collection of genomic DNA molecules amplified from a sample. Although libraries using any type of cloning vector, such as eukaryotic (e.g., yeast), procaryotic, or viral vectors, can be employed in the methods of the invention, the methods are particularly useful for producing target solutions from YAC, BAC, P1, PAC or cosmid libraries.

Labeling of Sample Nucleic Acids

As noted above, sample the nucleic acids that are hybridized to the target nucleic acids are preferably labeled to allow detection of hybridization complexes. The sample nucleic acids may be detectably labeled prior to the hybridization reaction. Alternatively, a detectable label may be selected which binds to the hybridization product. At least two different nucleic acid samples are hybridized to the array, either simultaneously or serially. Thus, each nucleic acid sample is labeled with a separate and distinguishable label.

The particular label or detectable group attached to the target nucleic acids is not a critical aspect of the invention, so long as it does not significantly interfere with the hybridization of sample nucleic acids to the target element of the array. The detectable group can be any material having a detectable physical or chemical property. Such detectable labels have been well-developed in the field of nucleic acid hybridizations and in general any label useful in such methods can be applied to the present invention. Thus, a suitable label is any composition detectable by spectroscopic, photochemical, biochemical, immunochemical, electrical, optical or chemical means. Useful labels in the present invention include fluorescent dyes (e.g., fluorescein isothiocyanate, texas red, rhodamine, and the like) radiolabels (e.g., $^3$H, $^{125}$I, $^{35}$S, $^{14}$C, or $^{32}$P), enzymes (e.g., horse radish peroxidase, alkaline phosphatase and others commonly used in an ELISA).

The nucleic acids can be indirectly labeled using ligands for which detectable anti-ligands are available. For example, biotinylated nucleic acids can be detected using labeled avidin or streptavidin according to techniques well known in the art. In addition, antigenic or haptenic molecules can be detected using labeled antisera or monoclonal antibodies. For example, N-acetoxy-N-2-acetylaminofluorene-labeled or digoxigenin-labeled probes can be detected using antibodies specifically immunoreactive with these compounds (e.g., FITC-labeled sheep anti-digoxigenin antibody (Boehringer Mannheim)). In addition, labeled antibodies to thymidine-thymidine dimers can be used (Nakane et al. ACTA Histochem. Cytochem. 20:229 (1987)).

Generally, labels which are detectable in as low a copy number as possible (thereby maximizing the sensitivity of the assay) and yet are detectable above any background signal are preferred. A label is preferably chosen that provides a localized signal, thereby providing spatial resolution of the signal from each target element.

Labels that provide a difference in signal intensity based on sequence differences are preferred for use in the invention. Examples of such labels include labels attached to one or more specific nucleotides, whereby a difference in the frequency of occurrence of the labeled nucleotide(s) in different nucleotide sequences produce a difference in the hybridization signal. Labeled antibodies to specific nucleotide dimers would provide similar signal differences corresponding to sequence differences. Any conventional label can be tested to determine empirically the degree to which signal is affected by sequence differences.

The labels may be coupled to the DNA in a variety of means known to those of skill in the art. In a preferred embodiment, sample nucleic acids are labeled using nick translation or random primer extension (Rigby, et al. J. Mol. Biol., 113:237 (1977) or Sambrook, et al., Molecular Cloning—A Laboratory Manual, Cold Spring Harbor Laboratory, Cold Spring Harbor, N.Y. (1985)) or by using labeled primers in an amplification reaction.

Hybridization of Sample Nucleic Acids to Target Nucleic Acids

The nucleotide sequence differences in at least two nucleic acid samples are compared by hybridizing the labeled nucleic acids from each sample to a nucleic acid arrays. The hybridization signal intensity, and the ratio of intensities, produced by the labeled nucleic acids on each of the target elements is determined. Comparison of the signal intensity ratios among target elements permits detection of one or more sequence differences between the samples.

Standard hybridization techniques are used to probe a target nucleic acid array. See, e.g., U.S. Pat. No. 5,830,645, issued to Pinkel et al. on Nov. 3, 1998. Suitable methods are described in references describing CGH techniques (Kallioniemi et al., Science 258:818-821 (1992) and WO 93/18186). Several guides to general techniques are available, e.g., Tijssen, Hybridization with Nucleic Acid Probes, Parts I and II (Elsevier, Amsterdam 1993). For a descriptions of techniques suitable for in situ hybridizations see, Gall et al. Meth. Enzymol., 21:470-480 (1981) and Angerer et al. in Genetic Engineering: Principles and Methods Setlow and Hollaender, Eds. Vol 7, pgs 43-65 (plenum Press, New York 1985).

Generally, nucleic acid hybridizations comprise the following major steps: (1) immobilization of target nucleic acids; (2) prehybridization treatment to increase accessibility of target nucleic acids, and to reduce nonspecific binding; (3) hybridization of sample nucleic acids to the target nucleic acids; (4) posthybridization washes to remove nucleic acid fragments not bound in the hybridization and (5) detection of the hybridized nucleic acid fragments. The reagent used in each of these steps and their conditions for use vary depending on the particular application.

In some applications it is necessary to block the hybridization capacity of repetitive sequences. A number of methods for removing and/or disabling the hybridization capacity of repetitive sequences are known (see, e.g., WO 93/18186) and are described above in the general description of CGH.

Detection

Standard methods for detection and analysis of signals generated by labeled probes can be used. The particular methods will depend upon the labels used in the probes. Generally, fluorescent labels are preferred. When fluorescent labels are employed, nucleic acid arrays can be imaged in a fluorescence microscope with a polychromatic beam-splitter to avoid color-dependent image shifts, according to standard techniques (see, e.g., U.S. Pat. No. 5,830,645, issued Nov. 3, 1998 to Pinkel et al). The different color images are acquired by an optical detector, and the digitized images are stored in a computer. A computer program is then used to analyze the signals produced by the array.

Two types of optical detectors, photomultiplier tube (PMT) and charged coupled devices (CCD), are commonly used in microarray imaging systems at the current time. In PMT-based systems, a point source of light, for example a focused laser beam, is scanned over the array, causing emission of light from the array. The emitted light is detected by the PMT and converted to an electrical current, and an image of the array is built up by associating the output of the PMT with the position of the scanning beam as it moves over the array. In common CCD systems, the entire array, or portion thereof, is illuminated and the emitted light is imaged onto the CCD chip. Thus, light is quantitatively measured from multiple points of an array simultaneously. CCD systems have potential advantages over PMT systems in several major areas: (1) the output of a CCD is linearly proportional to light intensity over a wider dynamic range than a PMT; (2) the efficiency of detecting light (quantum efficiency) is higher; and (3) the mechanical design is simpler since it is not necessary to scan the illumination beam.

In order to obtain the full benefits of CCD imaging, one needs to overcome several significant problems in optical design. These include minimizing or properly correcting for residual spatial variations in the sensitivity of the imaging system over the surface of the array, design of filters to obtain adequate spectral discrimination of multiple wavelengths and to reduce stray light, and reduction of "ghost" images due to reflections within the optical system.

Figure 3:
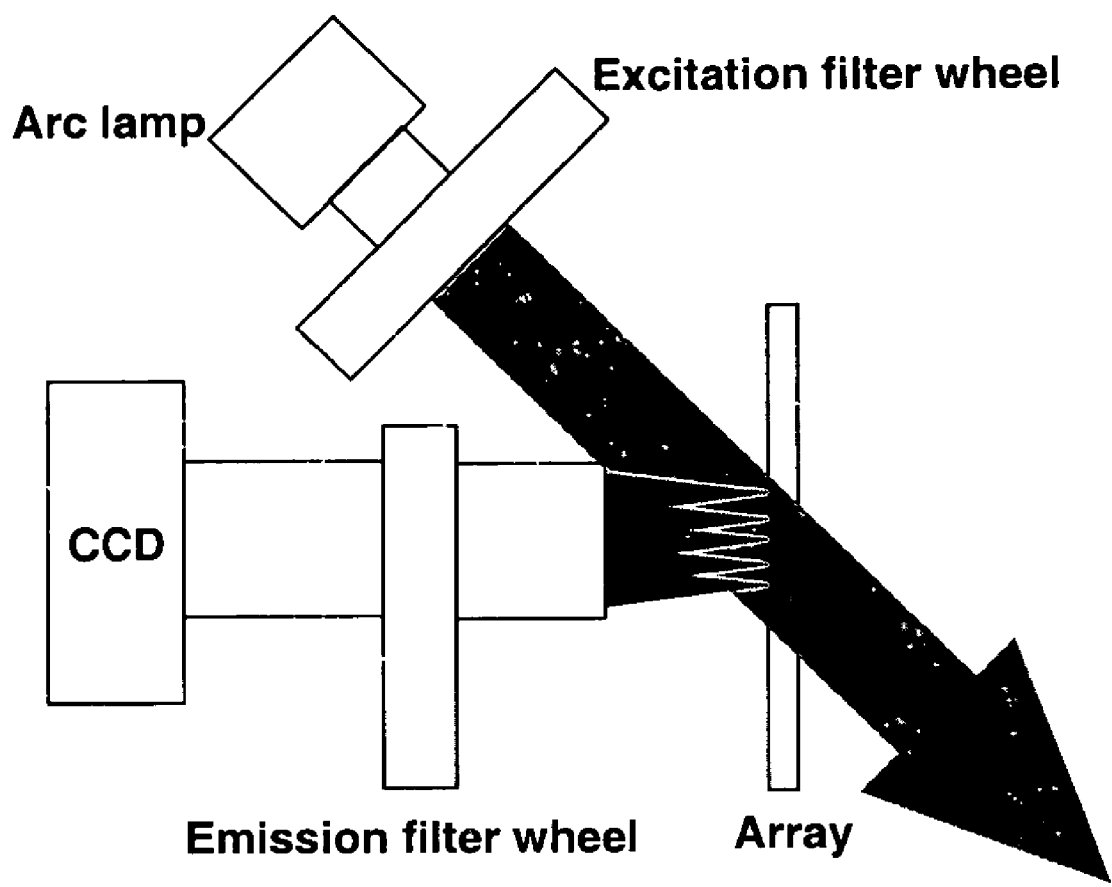
FIG. 3 shows a schematic overview of an array imaging system. An array on transparent substrate is illustrated. In some cases arrays are printed on highly reflective substrates so that essentially all of the excitation light is reflected from the array. Even if transparent substrates are used, approximately 10% of the excitation light may be specularly reflected from the array.
Figure 4:
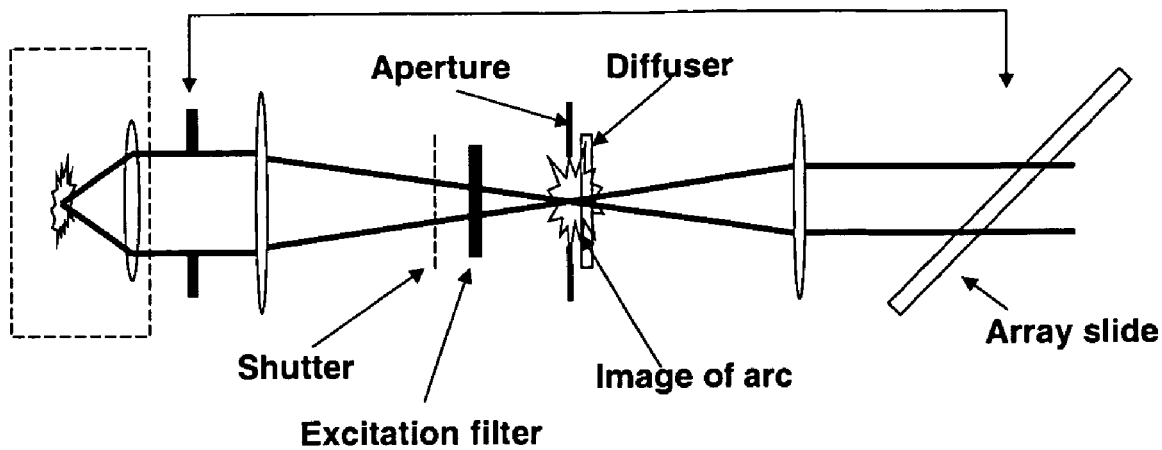
FIG. 4 shows a schematic overview of the excitation optics for a preferred array imaging system.

An overview of the major optical components of a preferred system is shown in FIG. 3. See, also, co-pending U.S. application Ser. No. 10/850,986 (filed May 20, 2004 by Albertson and Pinkel). Fluorescence excitation light is supplied by a mercury arc lamp from a conventional fluorescence microscope (Nikon). The light is collected by a condenser lens and focused to an image with a 150 mm focal length quartz lens (FIG. 4). Prior to focus, the light passes through a filter to select the desired excitation wavelength band. The filter is carried in a filter wheel so that it can be replaced by a different filter under computer control. The angle of convergence of the excitation light beam is less than 10 degrees so that the pass band of the filter is essentially constant for all of the light (see filter discussion below). The excitation light passes through an aperture at the location of the image of the arc. In order to improve the uniformity of the illumination at the location of the array, a diffuser plate is located in the opening of the aperture. This diffuser provides a 1 to 3 degree angular dispersion of the incident light. The excitation light then passes through a 200 mm focal length achromatic lens that is located at approximately its focal length from the aperture. This lens then puts an image of the arc at infinity. The array is placed at approximately the location where the back focal plane of the condenser lens in the lamp housing is in focus on the array. As shown in FIG. 3, the excitation light is incident on the array at approximately 45 degrees from the normal. The light does not come through the front lens of the detection optics, as is done in standard microscopes, because the excitation light will cause the lenses to fluoresce, which will cause background light in the image and degrade the accuracy of the measurements. For the same reason, the angle of incidence of the excitation light is chosen so that excitation light that is specularly reflected from the array does not enter the optics. Diffusely scattered light from the array surface does enter the lens and may cause difficulties, which are overcome as described below.

Figure 5:
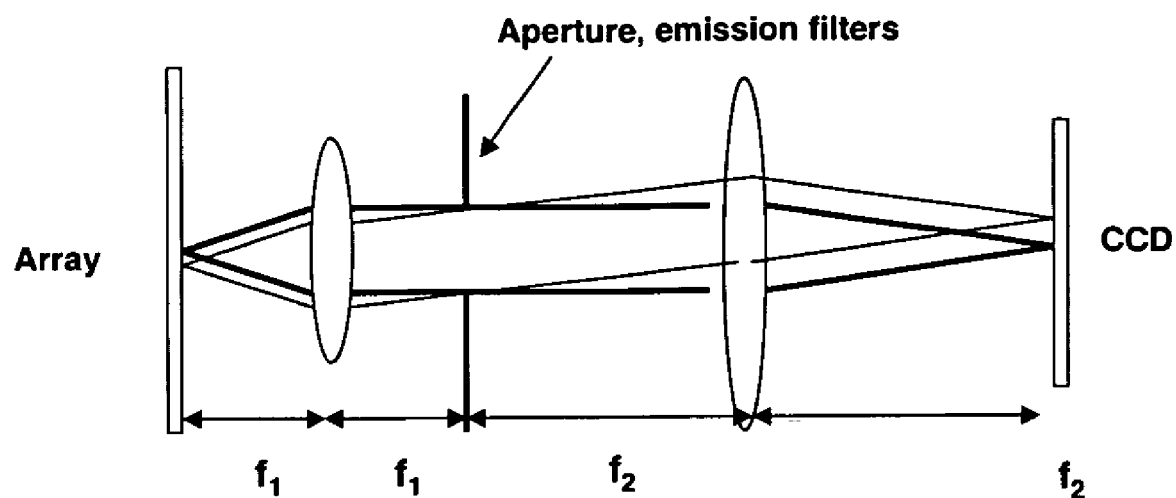
FIG. 5. shows a schematic overview of the detection optics for a preferred array imaging system. Light emitted from the array enters the first lens and is focused to infinity. An aperture and the emission filters are in the back focal plane of the first lens. The second lens takes this light and forms an image of the array on a CCD chip. The two lenses are separated by approximately the sum of their focal lengths.
Figure 6:
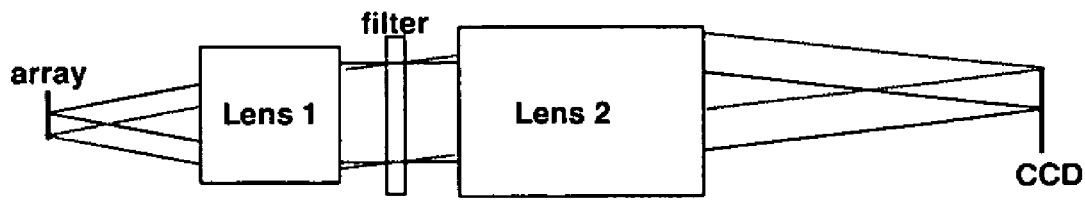
FIG. 6 shows preferred parameters for the detection optics of FIG. 5.
Figure 6:

The detection optics are designed to be telecentric (FIGS. 5 and 6). They consist of two well-corrected compound lenses that are separated by approximately the sum of their focal lengths. An adjustable aperture and the fluorescence emission filters are placed in the back focal plane of the first lens, which is approximately the front focal plane of the second lens. In this design, adjusting the aperture affects the intensity of the image uniformly over its entire area. The focal length of the front lens and the size of the area to be imaged are such that none of the light that is being properly imaged is incident on the emission filter at an angle greater than 10 degrees in order to assure that the spectral characteristics of all parts of the image are the same. In this instrument, in typical operation the radius of the object field is 9 mm or 18 mm, and the focal length of the first lens is 75 mm or 150 mm respectively, so the maximum angle for light from the image to pass through the filter is ~7 degrees. These two lenses have been designed to correct geometric and chromatic aberrations, and the image field is flat. It is not necessary to adjust focus when acquiring images of fluorochromes that emit between 450 and 750 nm. All of the lens surfaces are anti reflection coated over this same wavelength range.

The image is acquired using a CCD camera with an anti-reflection coated entrance window and an anti-reflection coated chip.

Several considerations affect the design of the fluorescence emission filter. First, utilization of this instrument typically requires acquiring images of multiple fluorochromes and analyzing them together. Preferably, all of the images are properly registered, that is there is no optical shift in the image of one of the fluorochromes in the specimen compared to the others. Part of this is accomplished by the lens design, which, as stated previously, is chromatically corrected. However, if the emission filter is slightly wedge-shaped, such that its surfaces are not parallel, then the light that passes through it will be bent. When the filter is changed to view another fluorochrome, the new filter may have a different wedge, and so there will be a relative shift between the two images. Thus it is important that the filters be made so that their surfaces are as close to exactly parallel possible. Preferable, the apparent shift of an image of the same object at different wavelengths is <3 µm.

Second, it is preferable that none of the excitation light reach the CCD camera, because it will add background to the image. The interference filters that are now in common use are very good at blocking light that is traveling properly through the optics and is incident at near normal incidence on the filter surface. However the pass band of interference filters is sensitive to the angle of incidence, moving to lower wavelengths as the deviation from normal increases. There is almost no change for about 10 degrees or so, but after that, the shifts become significant. Some of the excitation light that is diffusely scattered from the array will enter the optics. This will occur over a wide range of angles. Some of this light will scatter off of the internal structure of the lens and be incident on the filter at a large angle from the normal. This light may then pass through the filter because it sees a pass band shifted to shorter wavelengths, and it may enter the second lens. It may then scatter from the structure of that lens, and some of it may reach the CCD and cause background. In one embodiment, this issue is addressed by using a compound emission filter design that consists of a set of interference coatings that define a pass band with very steep sides for the purposes described below. In addition, the filter contains a layer of absorbing glass that blocks transmission by a factor of 100 or more at wavelengths shorter than the nominal pass band of the filter. Absorbance filters are not sensitive to the angle of incidence of the light. Thus excitation light incident on such a composite filter at large angle from the normal, which could pass through the interference portion of the filter, will be stopped by the absorption filter. This composite filter has somewhat less efficiency in transmitting light compared to a standard interference filter, but this is compensated for by the reduction in background light, which improves the signal to noise ratio in the images.

Third, some light will be reflected from the filter. This light will travel back to the array where it will be in focus if the optics are set up so that the array is in the front focal plane of the lens. It may be re-reflected from the array substrate. This multiply reflected light will be in focus on CCD camera, causing a ghost image of the array. Thus, it is preferable to minimize the reflection from the filter so the filter is designed to have very steep spectral characteristics at the edges of its pass band as determined by the interference coatings that are used in the filter. In addition, the filter has an anti-reflection coating on both surfaces to that is optimized for its pass band. Thus, this source of ghost images is reduced. In addition, the optics are set up so that they are not exactly telecentric. Thus, ghost images of the array due to reflections are out of focus in the image, and background subtraction procedures in the image analysis software corrects for the presence of this slight amount of reflected light.

All publications cited herein are hereby expressly incorporated by reference.

This invention is further illustrated by the following specific, but non-limiting, examples. Procedures that are constructively reduced to practice are described in the present tense, and procedures that have been carried out in the laboratory are set forth in the past tense.

EXAMPLES

The following example is offered to illustrate, but not to limit, the claimed invention.

Example 1

Preparation of Target Solutions from BAC Clones by Lilation-Mediated PCR

This study addressed the problems of the continual need to grow BACs for DNA and the problems with viscosity in printing BAC DNA by generating a PCR representation of the BAC. Ligation-mediated PCR was used to produce large amounts of BAC DNA that could be used to make low-viscosity target solutions suitable for robotic spotting. In this procedure, the DNA was first digested with MseI, an enzyme with a 4-base recognition site to maximize the frequency at which the DNA is cut. An adapter was then ligated to the digested DNA and used to prime an initial PCR amplification. To make DNA for spotting, a second PCR amplification was performed using the first PCR product as template.

DNA Isolation and Restriction Enzyme Digest

Cultures of BAC clones from the RP11 human BAC library were prepared by inoculating 5 µl LB with 1 µl from individual glycerol stocks and allowed to grow overnight. The overnight cultures were maintained at 4° C. for 8 hrs prior to use. Then, 25 mL cultures were prepared by inoculating LB medium with 200 µl of each overnight culture. These cultures were incubated at 37° C. in a shaking incubator for 14-16 hr ($OD_{600}$=0.25-0.35). BAC DNA was isolated from the cultures by standard alkaline lysis followed by purification over Qiagen Mini™ columns. Buffer volumes were increased as recommended by the manufacturer and routine yields were approximately 5 µg of DNA/25 ml culture. The DNA was minimally contaminated by the host bacterial genomic DNA (~6%, based on number of E. coli sequence reads from a shotgun library prepared from the BAC DNA).

Isolated BAC DNA (20 ng to 300 ng) was digested with MseI in a 5 µl reaction mixture containing 1.5 µl DNA, 0.2 µl 10×One-Phor-All-Buffer-Plus™ (Pharmacia), and 1 µl MseI (New England Biolabs; diluted to 2 units/µl in 10×One-Phor-All-Buffer-Plus™). After incubation at 37° C. overnight, the DNA was diluted to a final concentration of 1 ng/µl in water.

Ligation-Mediated PCR

Adapter (primer 1), 5'-AGT GGG ATT CCG CAT GCT AGT-3' (SEQ ID NO:1); containing a 5' aminolinker and primer oligonucleotide (primer 2), 5' TAA CTA GCA TGC-3' (SEQ ID NO:2) was annealed to the TA overhangs that were created by digestion of the DNA with MseI by incubating 1 µl of the MseI digest product (1 ng/µl) with 0.5 µl of each primer (100 µM), 0.5 µl of 10×One-Phor-All-Buffer-Plus™ (Pharmacia) and 5.5 µl of $H_2O$. Annealing was initiated at 65° C. for 1 min. to inactivate the restriction enzyme, and then the temperature was lowered to 15° C., with a ramp of 1.3° C./min. Once the temperature reached 15° C., 1 µl ATP (10 mM) and 1 µl T4 DNA ligase (5 units/µl, Boehringer Mannheim) were added. The mixture was then incubated overnight.

Primary PCR was carried out as follows. 3 µl of 10×PCR buffer (Boehringer Mannheim, Expand Long Template™, buffer 1), 2 µl of dNTP's (10 mM), and 35 µl of water was added. The temperature was raised to 68° C. for 4 min to remove primer 2, and then a fill-in-reaction was carried out for 3 min after addition of 1 µl (3.5 units) of a mixture of Taq and Pwo DNA polymerases (Boehringer Mannheim, Expand Long Template™). Thermal cycling was carried out in a Perkin-Elmer Gene Amp PCR™ system 9700 block for 14 cycles of 94° C. for 40 sec, 57° C. for 30 sec, and 68° C. for 75 sec; followed by 34 cycles of 94° C. for 40 sec, 57° C. for 30 sec, 68° C. for 105 sec; and a final cycle of 94° C. for 40 sec, 57° C. for 30 sec and 68° C. for 5 min.

To make DNA for spotting, 1 µl of DNA from this primary PCR (approximately 100 ng/µl) was re-amplified in a 100 µl reaction containing 4 µM primer 1, 1×TAQ-buffer II™ (Perkin Elmer), 0.2 mM dNTP mix (Boehringer Mannheim), 5.5 mM $MgCl_2$ (Perkin Elmer), and 2.5 units Amplitaq Gold™ (5 units/µl, Perkin Elmer). The polymerase was activated by incubation at 95° C. for 10 min in a Perkin-Elmer Gene Amp™ PCR system 9700 block, and then thermal cycling was carried out for 45 cycles of denaturation at 95° C. for 30 sec, annealing at 50° C. for 30 sec, and polymerization at 72° C. for 2 min., followed by a final extension at 72° C. for 7 min.

Preparation of Target Solutions

The volume of each amplification reaction (containing ~10 µg DNA/100 µl) was reduced to ~50 µl by incubation in a fan oven (Techne Hybridizer HB-1D) at 45° C. for 75 min. The DNA was precipitated by addition of 2.5 volumes of ethanol and one-tenth volume of 3M sodium acetate. The solution was mixed and then centrifuged at 4,000 rpm for 75 min. The supernatant was removed and the pellet washed with 70% ethanol and then centrifuged again at 4,000 rpm for 45 min. The supernatant was removed, and the pellet was allowed to air dry. The DNA was then resuspended in 5 µl of 20% vol/vol DMSO in water.

Using this procedure, as many as 10,000 aliquots of spotting solution could be prepared from 100 ng of BAC DNA.

Example 2

Arraying of Target Solutions

Target solutions were printed on a substrate using a print head with multiple, closely-spaced printing tips. The printing tips were dipped into target solutions in 864-well microtiter plates, which permitted spacing the pins on 3 mm centers. The print head contained 16 pins (in a 4×4 arrangement) that produces 12 mm×12 mm arrays. Target elements were printed on approximately 150 µm centers.

The printing pins were made from quartz capillary tubes that were tapered toward the tip. A typical design had a 75 µm inside diameter tube that narrowed to a 25-50 µm opening at the tip. The pins were individually spring-mounted in the print head so that the pins could move independently. Each was connected by flexible tubing to a manifold that supplied pressure or vacuum as required. Each print cycle began with cleaning the pins by drawing cleaning solutions through them under vacuum. They were then dried in an air blast and dipped into the microtiter plate. A slight vacuum was applied to draw target solutions into the pins. The print head was then moved along a gantry in the X direction while the array substrates, which were mounted on a precision stage, were moved in the Y direction so that the printhead could be placed over any desired location on the substrates. The print head was then lowered to contact the slides for printing. Three replicate target elements were printed for each target nucleic acid to allow averaging of hybridization signal across the replicates. 476 full genomic arrays containing triplicate copies of each of 2464 clones (~1.4 Mb resolution in a mammalian genome), could be printed in 13 hours. The arrays used in Example 3 contained about 1800 clones, each printed in triplicate.

The above procedure was carried out using a variety of substrates, including aminosilane, poly-lysine, and chromium.

After spotting, the arrays were typically dried overnight (although this is not necessary) and then placed in a UV Stratolinker 2400™ (Stratagene) and treated twice with 65 mJoules to improve attachment of the DNA to the substrate.

Results

Figure 2:
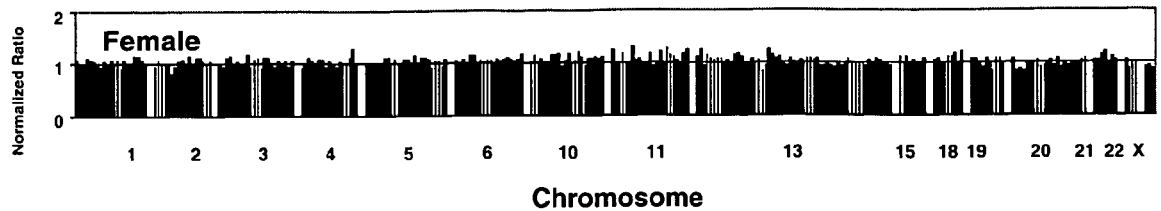
FIG. 2 shows the results of CGH of DNA from the breast cancer cell line BT474 (labeled with FITC-dCTP) and normal female DNA (labeled with Cy3-dCTP) to an array containing target elements prepared by ligation-mediated PCR from about 400 BAC clones that sample the human genome. Each bar represents the hybridization signal ratio obtained for a clone, and the clones are grouped by order on each chromosome. Chromosome numbers are indicated on the X-axis. Panel A illustrates that, as expected, the ratio of the hybridization signal for two samples of normal female DNA is essentially constant for all targets. The results in panel A are normalized to about 1.0. Panel B shows the (non-normalized) ratios of the signals observed for the BT474:normal DNA hybridization and indicates that copy number variations in BT474 DNA, especially those present on chromosome 20, are readily detectable in this system.
Figure 2:
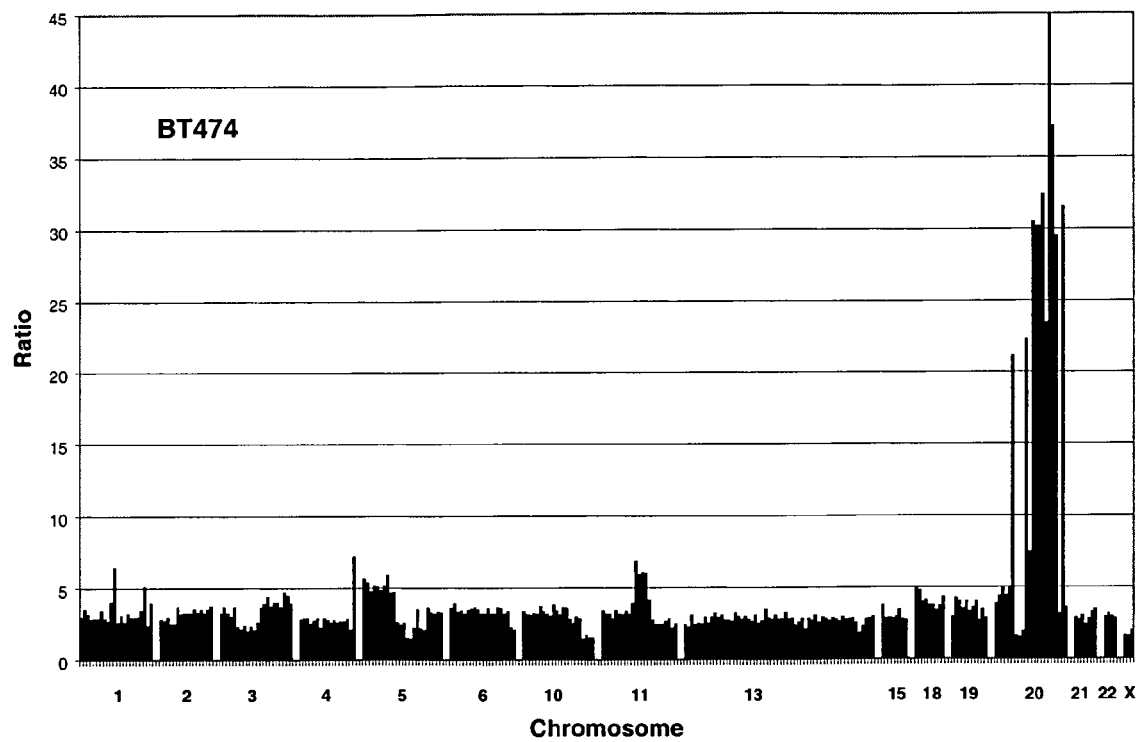

Side-by-side hybridization of arrayed BAC DNA and DNA prepared from the same BACs by ligation-mediated PCR yielded the same results (see FIG. 1), indicating that the DNA prepared by ligation-mediated PCR was representative of the starting BAC DNA. FIG. 2 shows the results of CGH to genome scanning array containing DNA from 400 BAC clones prepared by ligation-mediated PCR and arrayed as described in this example. FIG. 2 demonstrates that the methods described herein produce arrays that are representative of the starting nucleic acids.

Example 3

Detection of Sequence Differences Between Genomes Using Array CGH

Study Protocol

The sequence differences between *M. musculus* (strain NIH) and *M. Spretus* were detected by performing CGH using two genomic DNA samples, one from an individual from one of the parental mice, NIH, in the data presented below, and the other from an individual resulting the backcross of an F1 individual with NIH. The genetic content of the F1, a cross between NIH and Spretus mice, was half Spretus and half NIH at all chromosomal locations. The chromosomes of the backcross mice were a mosaic of the genetic content of the two strains (due to crossover events during meiosis). Thus, these mice were either homozygous for NIH or heterozygous for NIH and Spretus DNA for a genomic locus. Array CGH was carried out to distinguish regions of homozygosity and heterozygosity in backcross mice. These regions of heterozygosity represent an average sequence divergence of 1% or less.

The basic procedure was similar to standard array CGH, as described in Examples 1 and 2. Both test and reference genomes were normal from the standpoint of copy number. The arrays contained BAC clones and were printed on chromium-coated slides, essentially as described above.

The genomic DNAs, 300 ng, were labeled with Cy3 and Cy5 using random primer labeling using the BioPrime (GIBCO) kit with some modifications. The reaction used final concentrations of 40 µM of Cy3- or Cy5-labeled dCTP, 40 units Klenow polymerase, 0.2 mM each of unlabeled dATP, dGTP and dTTP, and 0.05 mM unlabeled dCTP and 20 µl of random primer mixture from the kit in a final volume of 50 µl. The DNA was denatured in random primer buffer prior to addition of the enzymes and nucleotides. The labeling reaction proceeded over night, and the labeled DNA was separated from the other reaction components using a Microcon Sephadex column. The two labeled DNAs were mixed and 50 µl of unlabeled mouse Cot-1 DNA, 1 µg/µl according to the manufacturer, added and the combined DNAs were ethanol precipitated.

The precipitated DNAs were resuspended in a hybridization buffer containing 10% dextran sulfate, 50% formamide, 2×SSC, and 4% SDS. This mixture was heated to 70° C. to denature the DNA, and then held at 37° C. for 1-2 hours to allow blocking of the repetitive sequences by the Cot-1 DNA. The hybridization was performed by making a well around the array with rubber cement and first filling the well with ~50 µl of hybridization buffer without DNA in order to wet the slide. Most of this was removed from the well and the hybridization mixture added. The array was placed in a sealed environment at 37° C. to prevent evaporation of the hybridization mixture and slowly rocked (about 1-2 cycles/minute) in order to slowly transport the hybridization mixture over the array. The hybridization proceeded over two nights.

After hybridization, the hybridization mix was quickly removed from the array by a flowing stream of PN buffer (0.1 M sodium phosphate pH~8 with 0.1% NP40), and then washed for 15 minutes in 50% formamide, 2×SSC at 45° C., and finally in PN buffer for 15 minutes at room temperature. The excess liquid was drained from the array and a 90% glycerol, 10% phosphate buffer containing the DNA stain DAPI was applied to the array. The DAPI stained the DNA in the array elements so that they could be detected by the imaging system.

The genomic DNAs in the experiments consisted of: (1) test DNA that from F1 generation crosses between Spretus mice and NIH mice; (2) test DNA from backcrosses between the F1 mice as in #1 and NIH mice, and (3) reference DNA from NIH mice, and 4) reference DNA from Spretus Glasgow mice. Measurement typically involved labeling the test genomic DNA with Cy3 and the reference with Cy5. However in some cases the labeling was reversed. The arrays employed in this study contained about 1800 target elements produced, as, described above, from a publicly available genomic library prepared from C57B16 mice (Library RP 23, from Roswell Park Cancer Institute).

After hybridization, the arrays were imaged using the preferred CCD detection system described above. An image of the DAPI, Cy3 and Cy5 signals was obtained. The images were analyzed using the program SPOT (Jain et al 2002). This program uses the DAPI image of the array to identify the locations and boundaries of the array elements, and then measures the Cy3 and Cy5 signals within these boundaries. The signals are corrected for local background. The ratio for each array element is calculated as the ratio of the total background-corrected Cy3 fluorescence divided by the total background-corrected Cy5 fluorescence for an array element. The program calculates the linear ratio and the log2 of the ratio for each spot, as well as other parameters such as the per pixel correlation of the Cy3 and Cy5 signals. Signals on array elements must pass quality control criteria or they are discarded. These include having a correlation >0.8 and having a sufficiently high Cy3 and Cy5 fluorescence signal compared to the DAPI signal. The average and standard deviation of the log2 ratios of the replicate array elements were calculated. If the standard deviation exceeded 0.2, or only one array element of the triplicate survived the quality control tests, data from that clone was discarded. The data used for the analysis was the average of the log2 ratios.

Statistical Analysis

The changes in fluorescence ratio were directly visible to an observer. However, statistical analysis allows more optimal assessment of the variation, especially determination of the boundaries between parts of the genome with different composition. This analysis was performed using the method of Fridlyand et al. (described in detail below in the section entitled "Hidden Markov Models Approach to the Analysis of Array CGH Data." The analysis uses Hidden Markov models to determine whether the fluorescence ratio for a given target element (i.e., a given clone) is most consistent with it being in one of two ratio levels. One ratio level indicates binding to two copies of NIH sequences (i.e., homozygous for NIH), and the other ratio level indicates binding to one copy of NIH and one copy of Spretus (i.e., heterozygous for NIH). The separation between the two levels represents the differences in the means of the fluorescence ratios of clones assigned to the two levels.

Briefly, the following steps were carried out. Ratios for X-linked clones and clones that had a missing value in more than 25% of the samples were excluded from the analysis. Ratios from any clones that had not been mapped to genomic positions were also excluded. Ratios from duplicate and triplicate spots were averaged and certain data discarded as described above.

The averaged ratios were plotted with log2 fluorescence ratio (y-axis) versus clone (x-axis), ordered by position in the genome, to generate a fluorescence profile for F1 mice (where F1 DNA was co-hybridized to the array with NIH DNA) and for backcross mice (where backcross DNA was co-hybridized to the array with NIH DNA).

Each backcross profile was normalized by subtracting, the F1/NIH log2 ratio from the backcross/NIH log2 ratio. This subtraction partially corrects for various sources of consistent variation in the measurement process that are not due to the differences in the Spretus and NIH genomes.

The resulting data was fit to the two-state discrete time Hidden Markov Model, with each entire genomic profile treated as continuous set of data. See Fridlyand et al. (2004) Journal of Multivariate Analysis 90:132-153. The BIC model selection criterion with penalty constant of 1.5 (1 versus 2 states) was used to choose the number of states. This step determines if there are one or two ratio levels that characterize the segments of the genome. The standard deviation of the experimental noise was estimated. Then, the mean for each state was estimated by taking the median of all the clones belonging to a given state.

A smoothed value was assigned to each clone using the estimated mean of its state after removal of outliers and apparent noise fluctuations. Outliers were defined as clones that were five or more standard deviations away from the states' mean. Some of these outliers are due to DNA copy number differences between the two types of mice. Noise fluctuations were defined as clones that did not belong to a genomically contiguous set containing more than 5 clones assigned to the same state or covering a region longer than 5 Mb. The resulting smoothed Hidden Markov model results (normalized by F1) were plotted as log2 fluorescence ratio versus clone.

Multiple repeat hybridizations of several mouse genomic DNAs were performed, as have experiments where the dye in the two genomes was reversed. In all cases, the results were reproducible.

Results

The results of this analysis are shown in FIGS. 7-10. Panel A of each of the four figures shows the raw experimental data, and Panel B shows the statistically analyzed data. The vertical axis is the log2 of the fluorescence ratio, and the horizontal axis represents the order in the genome of each clone on the array. Vertical lines indicate boundaries of chromosomes.

Figure 7:
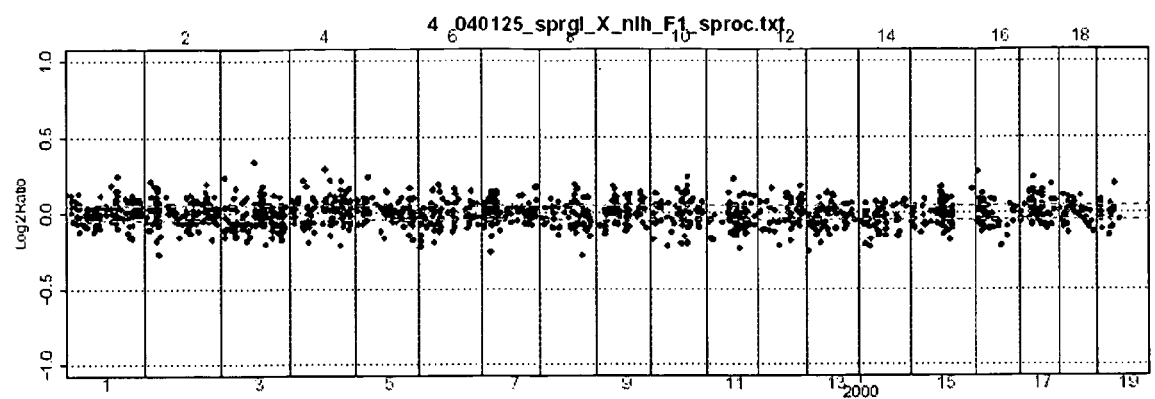
FIGS. 7-10 show the results of a study of sequence differences between two genomes using array CGH (see Example 3). The sequence differences between two strains of mice were detected by performing CGH using two genomic DNA samples, one from an individual from the F1 generation resulting from the cross of the two parental strains and the other from an individual resulting from the backcross of an F1 individual with one of the parental strains. The two parental strains were Spretus-Glasgow mice (which are outbred) and the line NIH, which is a Mus musculus strain.
Figure 7:
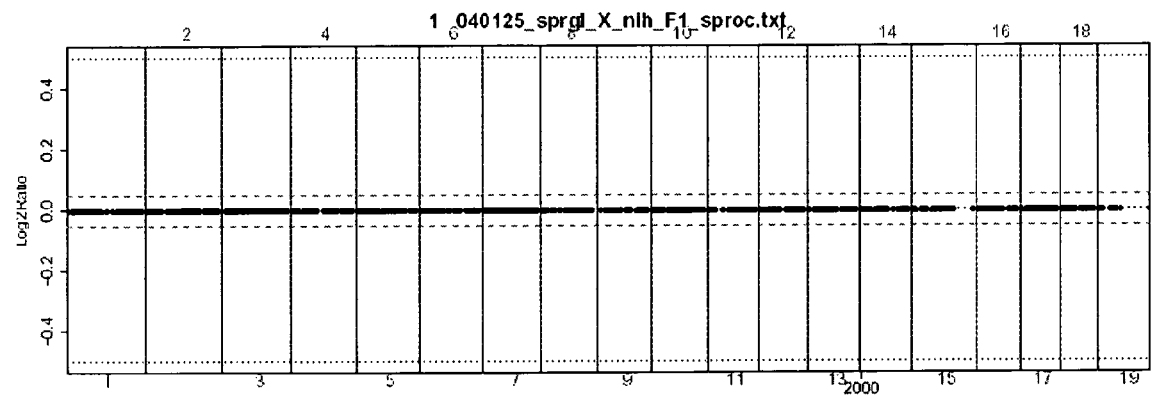
Figure 8:
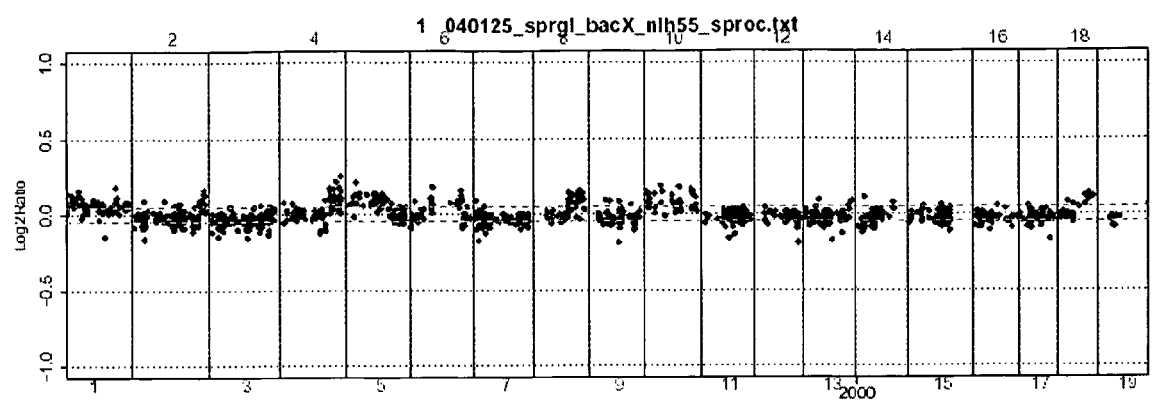
Figure 8:
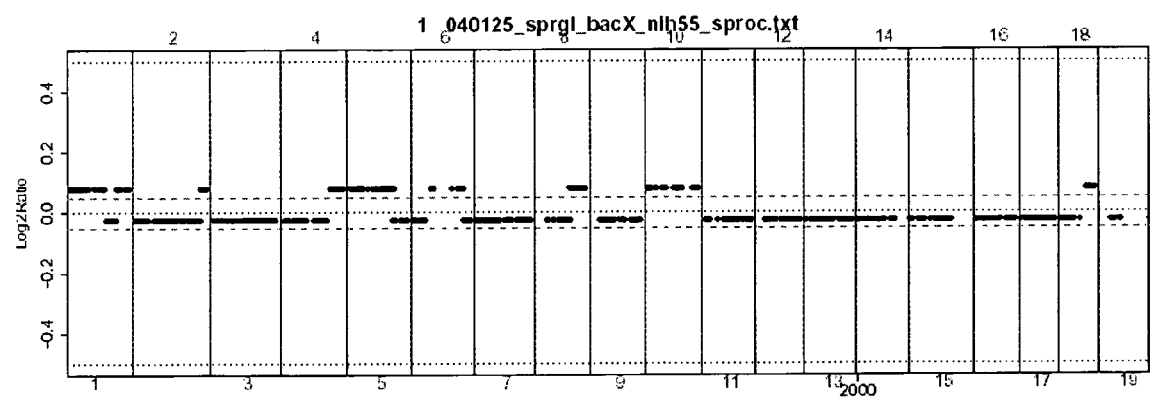
Figure 9:
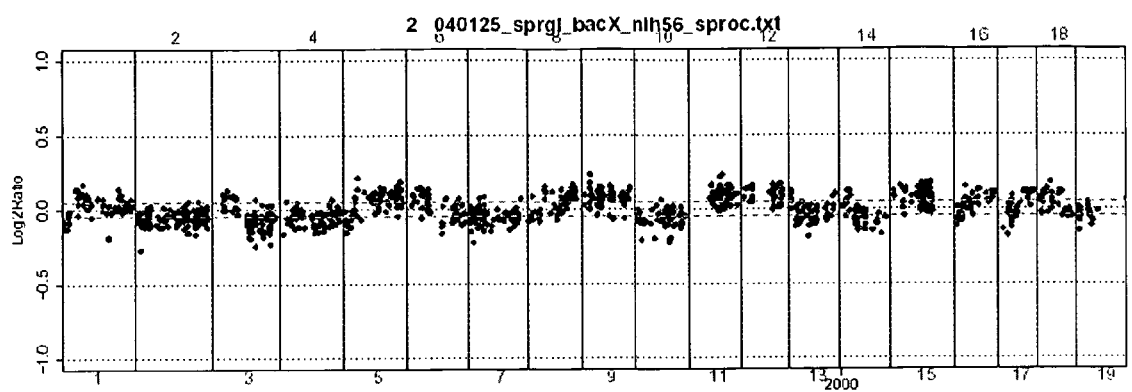
Figure 9:
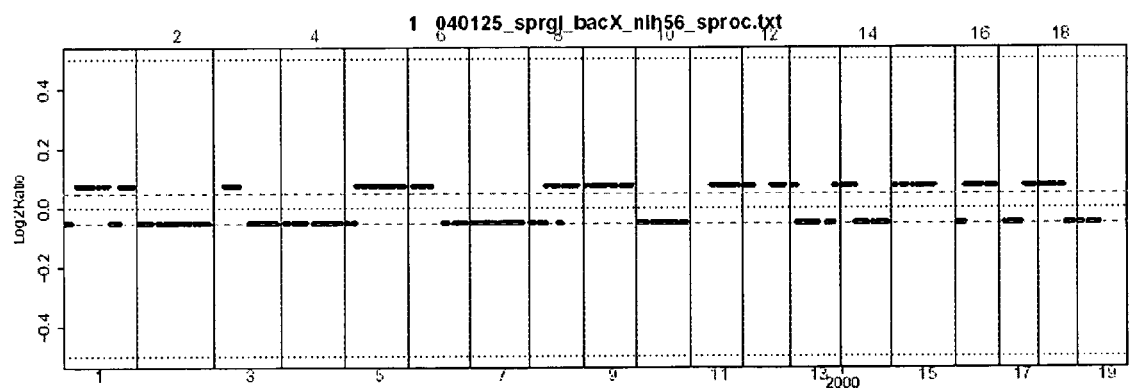
Figure 10:
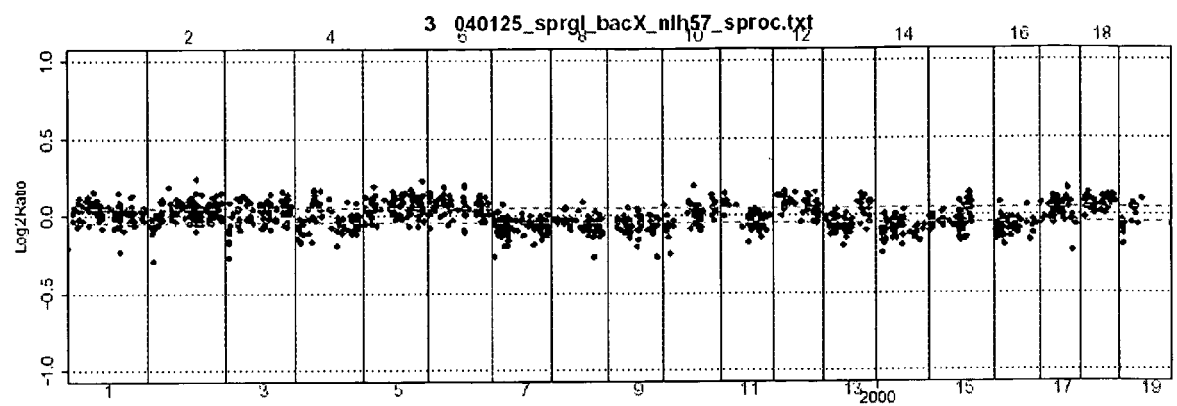
Figure 10:
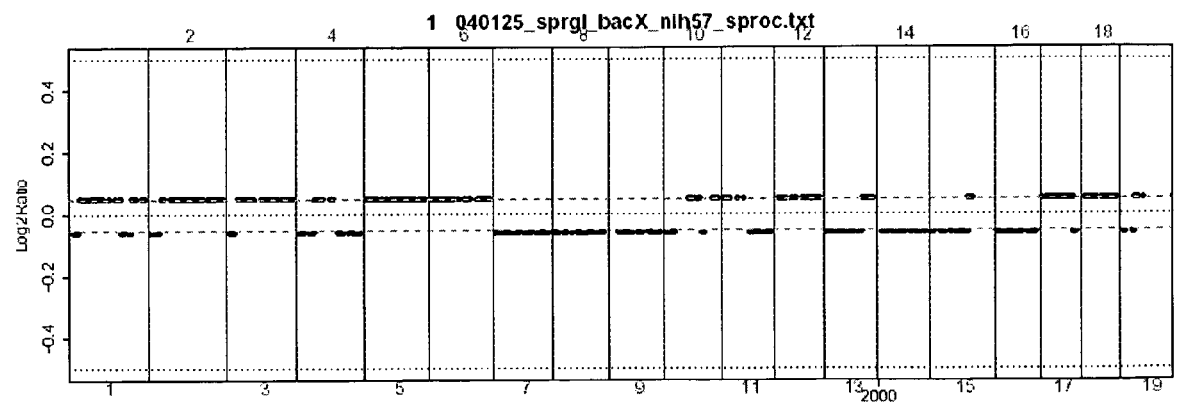

FIG. 7 shows the results for an F1 animal that has one copy of NIH sequence and one copy of Spretus sequence at all regions of the genome. The ratio is constant across the genome, and the analysis finds that all clones are at one ratio level. FIGS. 8-10 show the results from different backcross mice. Here, the ratios are not constant across the genome. Transitions between levels indicate a location in the genome where the genome changes from having two copies of NIH sequences to one copy of a Spretus sequence and one copy of NIH sequence. Each mouse has a different profile, as expected in backcross mice.

What is claimed is:

1. A method of detecting one or more nucleotide sequence differences in nucleic acid sequences in a first sample relative to nucleic acid sequences in a second sample, said method comprising:
 (a) labeling nucleic acids from each sample with a different label;
 (b) contacting the labeled nucleic acids from each sample with target nucleic acids, wherein either the labeled nucleic acids or the target nucleic acids, or both, have had repetitive sequences, if initially present, blocked and/or removed; and
 (c) comparing the intensities of the signals from labeled nucleic acids hybridized to the target nucleic acids to detect one or more nucleotide sequence differences between the samples.

2. The method of claim 1, wherein the labeled nucleic acids from each sample are contacted with the target nucleic acids simultaneously.

3. The method of claim 1, wherein said comparing comprises determining the ratio of signal intensity of the labeled nucleic acids from said first and second samples hybridized to each target nucleic acid.

4. The method of claim 3, wherein said comparing additionally comprises comparing the ratio for one target nucleic acid with the ratio for another target nucleic acid.

5. The method of claim 1, wherein the target nucleic acids comprise DNA molecules.

6. The method of claim 5, wherein the target nucleic acids comprise genomic DNA molecules.

7. The method of claim 1, wherein the samples are derived from different species.

8. The method of claim 1, wherein the samples are derived from the same species.

9. The method of claim 1, wherein the labeled nucleic acids from at least one sample comprise the genome of an organism.

10. The method of claim 1, wherein the one or more nucleotide sequence differences detected comprise loss of heterozygosity at one or more loci in the first sample relative to the second sample.

11. The method of claim 10, wherein the samples are derived from the same species.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 1
agtgggattc cgcatgctag t                                     21

<210> SEQ ID NO 2
<211> LENGTH: 12
<212> TYPE: DNA
<213> ORGANISM: Artificial
<220> FEATURE:
<223> OTHER INFORMATION: synthetic oligonucleotide primer

<400> SEQUENCE: 2
taactagcat gc                                               12